US009125862B2

(12) United States Patent
Muscatelli et al.

(10) Patent No.: US 9,125,862 B2
(45) Date of Patent: Sep. 8, 2015

(54) METHODS FOR THE TREATMENT OF PRADER-WILLI-LIKE SYNDROME OR NON-ORGANIC FAILURE TO THRIVE (NOFITT) FEEDING DISORDER USING AN AGONIST OF THE OXYTOCIN RECEPTOR

(71) Applicants: Francoise Muscatelli, Cedex Marseilles (FR); Maithe Tauber, Toulouse Cedex (FR); Fabienne Schaller, Cedex Marseilles (FR); Denise Thuilleaux, Hendaye (FR)

(72) Inventors: Francoise Muscatelli, Cedex Marseilles (FR); Maithe Tauber, Toulouse Cedex (FR); Fabienne Schaller, Cedex Marseilles (FR); Denise Thuilleaux, Hendaye (FR)

(73) Assignees: Institut National de la Sante et de la Rechereche Medicale (INSERM), Paris (FR); Universite de la Mediterranee, Marseilles (FR); CHU de Toulouse, Toulouse Cedex (FR)

( * ) Notice: Subject to any disclaimer, the term of this patent is extended or adjusted under 35 U.S.C. 154(b) by 0 days.

(21) Appl. No.: 14/472,680

(22) Filed: Aug. 29, 2014

(65) Prior Publication Data
US 2015/0005229 A1     Jan. 1, 2015

Related U.S. Application Data

(63) Continuation of application No. 13/699,649, filed as application No. PCT/EP2011/058590 on May 25, 2011, now Pat. No. 8,853,158.

(30) Foreign Application Priority Data

May 25, 2010   (EP) ..................................... 10305545
Sep. 21, 2010   (EP) ..................................... 10306004

(51) Int. Cl.
*A61K 38/11*    (2006.01)
*A61K 38/08*    (2006.01)

(52) U.S. Cl.
CPC ................. *A61K 38/08* (2013.01); *A61K 38/11* (2013.01)

(58) Field of Classification Search
None
See application file for complete search history.

(56) References Cited

U.S. PATENT DOCUMENTS

2004/0235956 A1   11/2004   Quay
2007/0032410 A1   2/2007   Quay et al.

OTHER PUBLICATIONS

Skuse. Arch. Dis. Childhood. 60: 173-178, 1985.*
Gowers et al.; "Treatment of anorexia nervosa in childhood and adolescence"; Psychiatry, vol. 4, No. 4, Apr. 2005, pp. 14-17.
Powell; "Nonorganic Failure to Thrive in Infancy: An Update on Nutrition, Behavior, and Growth"; Journal of the American College of Nutrition, vol. 7, No. 5, 1988, pp. 345-354.
Davies et al.; "Imprinted genes and neuroendocrine function"; Frontiers in Neuroendocrinology, vol. 29, No. 3, Jun. 1, 2008, pp. 413-427.
Hoybye; "Endocrine and metabolic aspects of adult Prader-Willi syndrome with special emphasis on the effect of growth hormone treatment"; Growth Hormone & IGF Research, vol. 14, No. 1, Feb. 2004, pp. 1-15.
Panahi et al.; "Bovine Colostrum in the Management of Nonorganic Failure to Thrive: A Randomized Clinical Trial"; Journal of Pediatric Gastroenterology and Nutrition, vol. 50, No. 5, May 2010, pp. 551-554.
Olszewski et al.; "Oxytocin as feeding inhibitor: Maintaining homeostasis in consummatory behavior"; Pharmacology, Biochemistry and Behavior, vol. 96, No. 1, Nov. 1, 2010, pp. 47-54.
McCarthy et al.; "Central nervous system actions of oxytocin and modulation of behavior in humans"; Molecular Medicine Today, vol. 3, No. 6, Jun. 1, 1997, pp. 269-275.
Uvnas-Moberg et al.; "Postnatal Oxytocin Injections Cause Sustained Weight Gain and Increased Nociceptive Thresholds in Male and Female Rats"; Pediatric Research, vol. 43, No. 3, Mar. 1, 1998, pp. 341-348.
Swaab et al. (J. Clin. Endocrinol. Metab. 80(2): 573-579, 1995)— Abstract only.
Schaller et al. Human Molecular Genetics. 19(24): 4895-4905, 2010.
Gimpl et al. Physiological Reviews 81(2): 630-683, 2001.
Marazziti et al. Clinical Neuropsychiatry 3(5): 302-321, 2006.
Skuse. Archives of Disease in Childhood. 60: 173-178, 1985.
Martin et al. Biol. Psychiatry 44. 1349-1352, 1998.
Cassidy et al. (Eur. J. Hum. Genetics 1-11, 2008).
Sasaki et al. Abstracts/Neuroscience Research 68S: e416 (P3-n12), 2010.

* cited by examiner

*Primary Examiner* — Christine J Saoud
(74) *Attorney, Agent, or Firm* — Whitham, Curtis, Christofferson & Cook, P.C.

(57) ABSTRACT

The present invention relates to a compound which is an agonist of the oxytocin receptor o for use in the treatment of a feeding disorder with early-onset. In a particular embodiment, the agonist of the oxytocin receptor is the oxytocin or an active fragment thereof.

8 Claims, 5 Drawing Sheets

Figure 1:
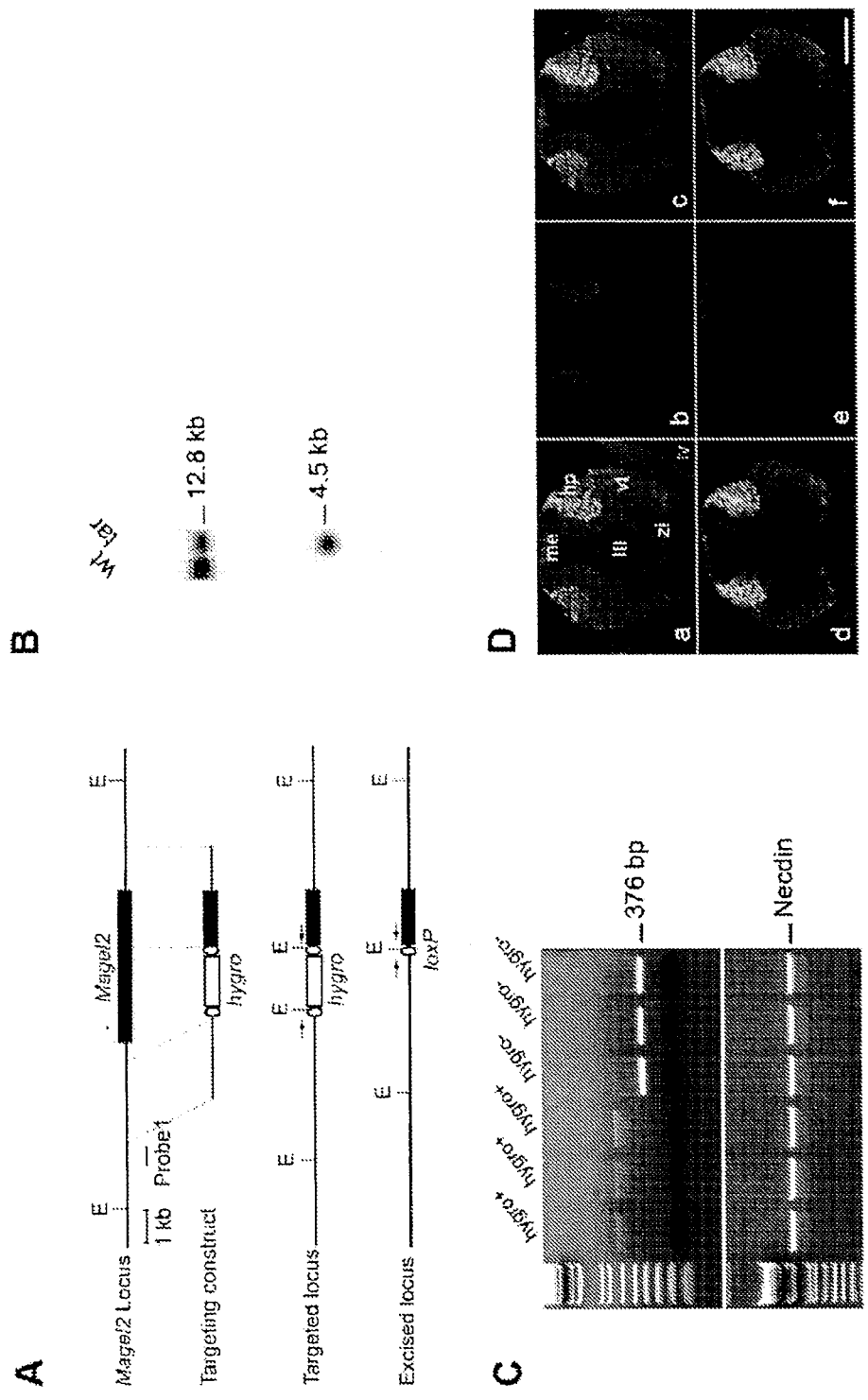

METHODS FOR THE TREATMENT OF PRADER-WILLI-LIKE SYNDROME OR NON-ORGANIC FAILURE TO THRIVE (NOFITT) FEEDING DISORDER USING AN AGONIST OF THE OXYTOCIN RECEPTOR

This application is a continuation application of U.S. Ser. No. 13/699,649, now U.S. Pat. No. 8,852,158, which was a Rule 137 of PCT/EP2011/058590 filed May 25, 2011.

FIELD OF THE INVENTION

The present invention relates to an agonist of the oxytocin receptor for use in the treatment of a feeding disorder with early-onset. In a particular embodiment, the agonist of the oxytocin receptor is the oxytocin or an active fragment thereof.

BACKGROUND OF THE INVENTION

Prader-Willi syndrome is a rare genetic disease (PWS; OMIM 176270). PW patients present a complex and progressive phenotype with mainly two phases. From birth until 2-3 years old, patients present feeding impairment with poor suckling and failure to thrive, a severe hypotonia, which tends later to disappear. Paradoxally, from this period they develop hyperphagic obesity. Patients also present many other symptoms such as respiratory distress, growth retardation due to growth hormone deficiency, hypogonadism, sleep disturbances, cognitive difficulties, skin picking, high pain threshold (Bittel and Butler 2005; Muscatelli 2008; Cassidy and Driscoll 2009) behavioural problems and psychiatric troubles probably related with social dysfunctions.

To date, no comprehensive pathophysiological mechanisms have clearly been identified, however much of the phenotype of PWS, including feeding problems, may be consistent with a hypothalamic defect (Swaab 1997). Human studies have mainly focused on hormone and neuropeptide dysregulations that might contribute to the phenotype in adult PW patients, but these dosages have been performed on plasma issued from patients and controls. In parallel, few studies have been reported on histological analysis from Prader-Willi patients' hypothalamus.

Genetically PWS results from the lack of expression of at least two imprinted genes located in the 15q11-q13 region, the paternal copy of these genes being expressed and their maternal copy being always silenced. It is accepted that PWS is a multigenic syndrome, involving more than one mutated gene (Goldstone 2004). From human genetic studies it has been proposed a role of SNORD116 (encoding for Small Nucleolar Orphan RNAs), in the hyperphagia, obesity and hypogonadism described in PWS (Sahoo, del Gaudio et al. 2008; de Smith, Purmann et al. 2009).

MAGEL2 is one of the candidate genes involved in Prader-Willi syndrome. Importantly, the mouse 7C chromosomal region has conserved synteny with the human 15q11-q13 region. Nearly all the content of genes is conserved, their order and their imprinted regulation. By creating and analysing a mouse model mutant deficient for Magel2, the inventors have shown that a Magel2-deficient mouse had an altered onset of suckling activity and subsequent impaired feeding, recalling the feeding phenotype seen in PW newborns. The hypothalamus of Magel2 mutant neonates showed a significant reduction of oxytocin content. Consistently, injection of a specific oxytocin receptor antagonist in wild type neonates recapitulated the feeding deficiency seen in Magel2 mutants. Importantly, a single injection of oxytocin, three to five hours after birth, rescued the phenotype of Magel2 mutant pups, allowing all of them to feed normally and to survive. Thus, this study revealed a role of Magel2 and an unexpected role of OT, via the OT receptor, in the initiation of feeding behaviour just after birth. Importantly, the lethal phenotype and the feeding behaviour deficiency observed in Magel2 KO, were rescued following an injection of 2 µg oxytocin, 3 to 5 hours after birth.

In parallel, the inventors showed that adult patients with PWS receiving a single intranasal administration of oxytocin have significantly less disruptive behavior, fewer conflicts and a strong tendency toward less sadness and less appetite.

SUMMARY OF THE INVENTION

The invention is based on the discovery that the administration of oxytocin is able to treat the behaviour deficits in infant and adult with Prader-Willi syndrome. Furthermore oxytocin injection or an agonist of the oxytocin receptor might be considered more generally for the treatment of a feeding disorder with early-onset in a patient.

Thus, the invention relates to an agonist of the oxytocin receptor for use in the treatment of a feeding disorder with early-onset in a patient.

A further object of the invention consists in a pharmaceutical composition that comprises at least one agonist as defined herein.

DETAILED DESCRIPTION OF THE INVENTION

Definitions

Throughout the specification, several terms are employed and are defined in the following paragraphs.

As used herein, the term "Prader-Willi syndrome" denotes a complex disease (OMIM 176270) which evolves with age. The essential clinical diagnostic criteria includes neonatal hypotonia and poor suck (0 to 2 years), a global developmental delay (2 to 6 years), hyperphagia due to the absence of normal satiety mechanisms leading to a severe obesity (6 to 12 years), learning difficulties, hypogonadism, behaviour and psychiatric problems (13 years through adulthood). Abnormalities of respiration are very frequent in PWS from birth. From the genetic point of view, PWS is a contiguous gene syndrome resulting from the absence of expression of the paternal copies of genes located in the 15q11-q13 region; the maternal copies of these genes being silenced trough genomic imprinting mechanism, it does result a complete absence of expression of these genes in PWS. The mutations observed in PW patients are mainly a large de novo deletion of the 15q11-q13 region from the paternal chromosome (70-80%) or a maternal uniparental disomy 15 (both chromosomes 15 are maternal in origin) (25-30%). A few PW patients (1-3%) have two chromosomes 15 of biparental inheritance but an imprinting mutation leads to a silencing of paternal genes involved in PWS.

As used herein, the term "oxytocin" denotes a mammalian nonapeptide expressed in the hypothalamus. Oxytocin, released in the bloodstream via the neurohypophysis, as a hormone is classical known for some physiological roles including stimulation of smooth muscle contractions in the uterus during labor and in mammary myoepithelium during nursing. Thus oxytocin facilitates birth and breastfeeding, respectively. This hormone also plays a role in a variety of other reproductive-related functions: modulation of estrous cycle length, follicle luteinisation in the ovary and ovarian steroidogenesis. In addition to these endocrine effects, oxytocin has a role as a neurotransmitter in the brain influencing various socio-sexual behaviours, including orgasm, social recognition, pair bonding, anxiety, trust, love, and maternal behaviours (see for example Ring R. H. et al., 2010). The "oxytocin receptor" belongs to the G-protein coupled receptor family. Its activity is mediated by G proteins which activate several different second messenger systems.

As used herein the term "feeding disorder with early-onset" denotes a disorder of the feeding behaviour at birth often named "failure-to-thrive syndrome" of some neonates in the most severe aspect. Feeding disorder with early-onset results in a suckling deficit during neonatal development, an absence of breast feeding and "abnormal" food intake.

Agonist and Uses Thereof

A first object of the invention relates to an agonist of the oxytocin receptor for use in the treatment of a feeding disorder with early-onset.

In another preferred embodiment, the agonist of the invention may be used for the treatment of feeding disorder from birth with suckling deficit.

In one embodiment, said agonist of the oxytocin receptor may be a low molecular weight agonist, e.g. a small organic molecule (natural or not).

The term "small organic molecule" refers to a molecule (natural or not) of a size comparable to those organic molecules generally used in pharmaceuticals. The term excludes biological macromolecules (e.g., proteins, nucleic acids, etc.). Preferred small organic molecules range in size up to about 10000 Da, more preferably up to 5000 Da, more preferably up to 2000 Da and most preferably up to about 1000 Da.

Typically said agonist may be used in combination with a compound against a feeding disorder with early-onset.

Agonists of the oxytocin receptor are well known in the state of the art (see for example, Manning M. et al., 2008).

In a particular embodiment, the agonist according to the invention may be the carbetocin or the demoxytocin (see for example Manning M. et al., 2008).

In a particular embodiment, the agonist according to the invention may be the [1-deamino-1-monocarba-2O-methyltyrosine]oxytocin (see for example Su L L. et al., 2007).

In a particular embodiment, the agonist according to the invention may be the WAY-267464 (sec for example Ring et al., 2009), WAY-VNA-932 or OPC-51803 (sec for example Pitt et al., 2004).

In another particular embodiment, the agonist according to the invention may be an oxytocin analogue (see for example patent applications WO2009122285) of formula I:

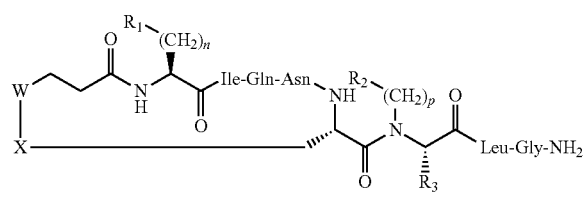

wherein:
n is selected from 0, 1 and 2; p is selected from 0, 1, 2, 3, 4, 5 and 6;
R1 is selected from aryl optionally substituted with at least one OH, F, Cl, Br, alkyl or O-alkyl substituent;
R2 is selected from R4, H, alkyl, cycloalkyl, aryl and 5- and 6-membered heteroaromatic ring systems;
R3 is selected from H and a covalent bond to R2, when R2 is R4, to form a ring structure;
R4 is Ci-6 alkylene moiety substituted with at least one O-alkyl, S-alkyl or OH substituent;
W and X are each independently selected from CH2 and S, but may not both be CH2; alkyl is selected from Ci_6 straight and C4-8 branched chain alkyl and optionally has at least one hydroxyl substituent; aryl is selected from phenyl and mono- or poly-substituted phenyl; with the proviso that when R2 is H, p is 1, R3 is H, n is 1 and W and X are both S, R1 is not 4-hydroxyphenyl; and solvates and pharmaceutically acceptable salts thereof.

In another particular embodiment, the agonist according to the invention may be a benzamide derivative (see for example patent application US2008275026).

In a preferred embodiment, the preferred agonist according to the patent application US2008275026 may be selected from the group consisting of:
4-(3,3-Dimethyl-butyl)-piperazine-1-carboxylic acid 2-methyl-4-(3-methyl-4,10-dihydro-3H-2,3,4,9-tetraaza-benzo[f]azulene-9-carbonyl)benzylamide;
4-(2-Cyclopropyl-ethyl)-piperazine-1-carboxylic acid 2-methyl-4-(3-methyl-4,10-dihydro-3H-2,3,4,9-tetraaza-benzo[f]azulene-9-carbonyl)benzylamide;
4-Cyclopropylmethyl-piperazine-1-carboxylic acid 3-methyl-4-(3-methyl-4,10-dihydro-3H-2,3,4,9-tetraaza-benzo[f]azulene-9-carbonyl)benzylamide;
4-Cyclopropylmethyl-piperazine-1-carboxylic acid 3-fluoro-4-(3-methyl-4,10-dihydro-3H-2,3,4,9-tetraaza-benzo[f]azulene-9-carbonyl)benzylamide;
4-(2-Hydroxymethyl-cyclopropylmethyl)-piperazine-1-carboxylic acid-2-methyl-4-(3-methyl-4,10-dihydro-3H-2,3,4,9-tetraaza-benzo[f]azulene-9-carbonyl)-benzylamide;
4-(3-Methyl-butyl)-piperazine-1-carboxylic acid 2-methyl-4-(3-methyl-4,10-dihydro-3H-2,3,4,9-tetraaza-benzo[f]azulene-9-carbonyl)-benzylamide;
4-Cyclopentylmethyl-piperazine-1-carboxylic acid 2-methyl-4-(3-methyl-4,10-dihydro-3H-2,3,4,9-tetraaza-benzo[f]azulene-9-carbonyl)benzylamide;
4-Cyclohexylmethyl-piperazine-1-carboxylic acid 2-methyl-4-(3-methyl-4,10-dihydro-3H-2,3,4,9-tetraaza-benzo[f]azulene-9-carbonyl)benzylamide;
4-Cyclopropylmethyl-piperazine-1-carboxylic acid 3-chloro-4-(3-methyl-4,10-dihydro-3H-2,3,4,9-tetraaza-benzo[f]azulene-9-carbonyl)benzylamide;
4-Cyclobutylmethyl-piperazine-1-carboxylic acid 3-chloro-4-(3-methyl-4,10-dihydro-3H-2,3,4,9-tetraaza-benzo[f]azulene-9-carbonyl)-benzylamide;
4-Cyclobutylmethyl-piperazine-1-carboxylic acid 2-methyl-4-(3-methyl-4,10-dihydro-3H-2,3,4,9-tetraaza-benzo[f]azulene-9-carbonyl)benzylamide;
4-(2-Cyclopropyl-ethyl)-piperazine-1-carboxylic acid 3-methyl-4-(3-methyl-4,10-dihydro-3H-2,3,4,9-tetraaza-benzo[f]azulene-9-carbonyl)benzylamide;
4-Pentyl-piperazine-1-carboxylic acid 2-methyl-4-(3-methyl-4,10-dihydro-3H-2,3,4,9-tetraaza-benzo[f]azulene-9-carbonyl)-benzylamide;
4-Hexyl-piperazine-1-carboxylic acid 2-methyl-4-(3-methyl-4,10-dihydro-3H-2,3,4,9-tetraaza-benzo[f]azulene-9-carbonyl)-benzylamide;

(R)-4-(2-Methyl-butyl)-piperazine-1-carboxylic acid 2-methyl-4-(3-methyl-4,10-dihydro-3H-2,3,4,9-tetraaza-benzo[f]azulene-9-carbonyl)benzylamide;
4-(2-Ethyl-butyl)-piperazine-1-carboxylic acid 2-methyl-4-(3-methyl-4,10-dihydro-3H-2,3,4,9-tetraaza-benzo[f]azulene-9-carbonyl)-benzylamide;
4-(2-Methyl-but-2-enyl)-piperazine-1-carboxylic acid 2-methyl-4-(3-methyl-4,10-dihydro-3H-2,3,4,9-tetraaza-benzo[f]azulene-9-carbonyl)benzylamide;
4-Cyclobutylmethyl-piperazine-1-carboxylic acid-3-methyl-4-(3-methyl-4,10-dihydro-3H-2,3,4,9-tetraaza-benzo[f]azulene-9-carbonyl)benzylamide;
4-Cyclobutylmethyl-piperazine-1-carboxylic acid 3-fluoro-4-(3 methyl-4,10-dihydro-3H-2,3,4,9-tetraaza-benzo[f]azulene-9-carbonyl)-benzylamide;
4-Cyclobutylmethyl-piperazine-1-carboxylic acid 2-fluoro-4-(3-methyl-4,10-dihydro-3H-2,3,4,9-tetraaza-benzo[f]azulene-9-carbonyl)benzylamide;
4-Cyclopropylmethyl-piperazine-1-carboxylic acid 2-fluoro-4-(3-methyl-4,10-dihydro-3H-2,3,4,9-tetraaza-benzo[f]azulene-9-carbonyl)benzylamide;
4-Cyclobutylmethyl-piperazine-1-carboxylic acid 4-(3-methyl-4,10-dihydro-3H-2,3,4,9-tetraaza-benzo[f]azulene-9-carbonyl)-benzylamide;
4-Cyclopropylmethyl-piperazine-1-carboxylic acid 2-ethyl-4-(3-methyl-4,10-dihydro-3H-2,3,4,9-tetraaza-benzo[f]azulene-9-carbonyl)-benzylamide;
4-Cyclobutylmethyl-piperazine-1-carboxylic acid 2-chloro-4-(3-methyl-4,10-dihydro-3H-2,3,4,9-tetraaza-benzo[f]azulene-9-carbonyl)-benzylamide;
4-Cyclopropylmethyl-piperazine-1-carboxylic acid 2-chloro-4-(3-methyl-4,10-dihydro-3H-2,3,4,9-tetraaza-benzo[f]azulene-9-carbonyl)benzylamide; and
4-Cyclobutylmethyl-piperazine-1-carboxylic acid 3-methoxy-4-(3-methyl-4,10-dihydro-3H-2,3,4,9-tetraaza-benzo[f]azulene-9-carbonyl)benzylamide.

In another particular embodiment, the agonist according to the invention may be a diazycycloalkanes derivative (see for example patent applications WO03016316).

In a preferred embodiment, the preferred agonist according to the patent application WO03016316 may be selected from the group consisting of:
5-(4-(4-cyclopropylmethylpiperazine-1-carbonylaminomethyl)-3-methylbenzoyl)-1-methyl-4,10-dihydropyrazolo[5,4-b][1,5]benzodiazepine;
5-(4-(4-benzylpiperazine-1-carbonylaminomethyl)-3-methylbenzoyl)-1-methyl-4,10-dihydropyrazolo[5,4-b][1,5]benzodiazepine;
5-(4-(4-(3-hydroxybenzyl)piperazine-1-carbonylamino methyl)-3-methylbenzoyl)-1-methyl-4,10-dihydropyrazolo[5,4-b][1,5]benzodiazepine;
5-(4-(4-(3-hydroxymethylbenzyl)piperazine-1-carbonylamino methyl)-3-methylbenzoyl)-1-methyl-4,10-dihydropyrazolo[5,4-b][1,5]benzodiazepine;
1-methyl-5-(3-methyl-4-(4-(4-picolyl)piperazine-1-carbonylasminomethyl)benzoyl)-4,10-dihydropyrazolo[5,4-b][1,5]benzodiazepine;
5-(4-(4-(2-hydroxyethyl)piperazine-1-carbonylaminomethyl)-3-methylbenzoyl)-1-methyl-4,10-dihydropyrazolo[5,4-b][1,5]benzodiazepine;
1-methyl-5-(3-methyl-4-(4-(3-(methylthio)propyl)piperazine-1-carbonylaminomethyl)benzoyl)-4,10-dihydropyrazolo[5,4-b][1,5]benzodiazepine;
5-(4-(4-(2-aminoethyl)piperazine-1-carbonylaminomethyl)-3-methylbenzoyl)-1-methyl-4,10-dihydropyrazolo[5,4-b][1,5]benzodiazepine; and
5-(4-(4-(2-hydroxyethyl)piperazine-1-carbonylaminomethyl)-3-methylbenzoyl)-1-methyl-4,10-dihydropyrazolo[4,5-c]pyrido[2,3-b][1,4]diazepine.

In another particular embodiment, the agonist according to the invention may be an oxytocin analogue (see for example patent applications WO03000692).

In a preferred embodiment, the preferred agonist according to the patent application WO03000692 may be selected from the group consisting of:
4-methyl-1-(N-(2-methyl-4-(2,3,4,5-tetrahydro-1,5-benzodiazepin-4-on-1-ylcarbonyl)benzylcarbamoyl)-L-thioprolyl)perhydro-1,4-diazepine;
4-methyl-1-(N-(2-methyl-4-(1-methyl-4,10-dihydropyrazolo[5,4-b][1,5]benzodiazepin-5-ylcarbonyl)benzylcarbamoyl)-L-thioprolyl)perhydro-1,4-diazepine;
4,4-dimethyl-1-(N-(2-methyl-4-(1-methyl-4,10-dihydropyrazolo[5,4-b][1,5]benzodiazepin5-ylcarbonyl)benzylcarbamoyl)-L-thioprolyl)perhydro-1,4-diazepinium iodide;
4-methyl-1-(N-(2-methyl-4-(5,6,7,8-tetrahydrothieno[3,2-b]azepin-4-ylcarbonyl)benzylcarbamoyl)-L-thioprolyl)perhydro-1,4-diazepine;
4-methyl-1-(N-(2-methyl-4-(5,6,7,8-tetrahydrothieno[3,2-b]azepin-4-ylcarbonyl)benzyloxy-carbonyl)-L-prolyl)perhydro-1,4-diazepine;
(4R)—N"-(2-chloro-4-(5,6,7,8-tetrahydrothieno[3,2-b]azepin-4-ylcarbonyl)benzylcarbamoyl)-4-methoxy-L-proline-N-methyl-N-(2-picolyl)amide; and
1-((4R)—N'-(2-chloro-4-(5,6,7,8-tetrahydrothieno[3,2-b]azepin-4-ylcarbonyl)benzylcarbamoyl)-4-methoxy-L-prolyl)-4-(1-pyrrolidinyl)piperidine.

In another particular embodiment, the agonist according to the invention may be a piperazine derivative (see for example patent applications WO2005023812 and EP1660501) of formula I:

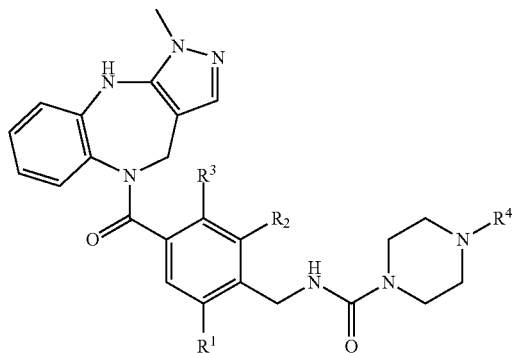

formula I wherein: R1, R2 and R3 are each independently selected from H, alkyl, F and Cl; and R4 is selected from formulae II, III and IV:

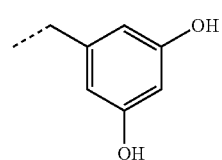

II

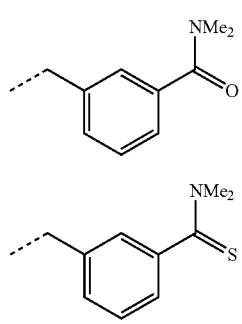

In a preferred embodiment, the preferred agonist according to the patent application WO03000692 may be selected from the group consisting of:
4-(3,5-Dihydroxy-benzyl)-piperazine-1-carboxylic acid 2-methyl-4-(3-methyl-4,10-dihydro-3H-2,3,4,9-tetraaza-benzo[f]azulene-9-carbonyl)-benzylamide;
4-(3,5-Dihydroxy-benzyl)-piperazine-1-carboxylic acid 2,6-dimethyl-4-(3-methyl-4,10-dihydro-3H-2,3,4,9-tetraaza-benzo[f]azulene-9-carbonyl)-benzylamide;
4-(3,5-Dihydroxy-benzyl)-piperazine-1-carboxylic acid 3-chloro-4-(3-methyl-4,10-dihydro-3H-2,3,4,9-tetraaza-benzo[f]azulene-9-carbonyl)-benzylamide;
4-(3,5-Dihydroxy-benzyl)-piperazine-1-carboxylic acid 2-fluoro-4-(3-methyl-4,10-dihydro-3H-2,3,4,9-tetraaza-benzo[f]azulene-9-carbonyl)-benzylamide;
4-(3-Dimethylcarbamoyl-benzyl)-piperazine-1-carboxylic acid 2-methyl-4-(3-methyl-4,10-dihydro-3H-2,3,4,9-tetraaza-benzo[f]azulene-9-carbonyl)-benzylamide; and
4-(3-Dimethylthiocarbamoyl-benzyl)-piperazine-1-carboxylic acid 2-methyl-4-(3-methyl-4,10-dihydro-3H-2,3,4,9-tetraaza-benzo[f]azulene-9-carbonyl)-benzylamide.

In another embodiment, the agonist of the oxytocin receptor may be an anti-oxytocin receptor antibody which binds to the oxytocin receptor or an anti-oxytocin receptor fragment thereof which bind to the oxytocin receptor (see for example Vela et al., 2010 and Serradeil-Le Gal et al., 2004 to find a test to discriminate between agonist and antagonist of oxytocin receptor).

Antibodies directed against the oxytocin receptor may be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against oxytocin receptor can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see e.g., U.S. Pat. No. 4,946,778) can be adapted to produce anti-oxytocin receptor single chain antibodies. Agonists useful in practicing the present invention also include anti-oxytocin receptor antibody fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to the oxytocin receptor.

Humanized anti-oxytocin receptor antibodies and antibody fragments therefrom can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

Then, for this invention, activator antibodies of the oxytocin receptor are selected.

In still another embodiment, the agonist of the oxytocin receptor may be selected from aptamers. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as E. coli Thioredoxin A that are selected from combinatorial libraries by two hybrid methods (Colas et al., 1996 and Serradeil-Le Gal et al., 2004 to find a test to discriminate between agonist and antagonist of oxytocin receptor).

Then, for this invention, activator aptamers of the oxytocin receptor are selected.

In another embodiment, the agonist of the oxytocin receptor is the oxytocin or an active fragment thereof.

In a preferred embodiment, said oxytocin fragment comprises at least 75% identity over said oxytocin, even more preferably at least 80%, at least 85%, at least 90%, at least 95%, at least 97%, at least 99%.

Oxytocyn of fragments thereof may be produced by any technique known per se in the art, such as, without limitation, any chemical, biological, genetic or enzymatic technique, either alone or in combination(s).

Knowing the amino acid sequence of the desired sequence, one skilled in the art can readily produce a relevant part of the said oxytocyn of fragments thereof, by standard techniques for production of peptide. For instance, they can be synthesized using well-known solid phase method, preferably using a commercially available peptide synthesis apparatus (such as that made by Applied Biosystems, Foster City, Calif.) and following the manufacturer's instructions.

Alternatively, oxytocyn of fragments thereof can be synthesized by recombinant DNA techniques as is now well-known in the art. For example, these fragments can be obtained as DNA expression products after incorporation of DNA sequences encoding the desired polypeptide into expression vectors and introduction of such vectors into suitable eukaryotic or prokaryotic hosts that will express the desired oxytocyn of fragments thereof, from which they can be later using well-known techniques.

Oxytocyn of fragments thereof can be used in an (e.g., purified) form or contained in a vector, such as a membrane or lipid vesicle (e.g. a liposome).

In specific embodiments, it is contemplated that the oxytocyn of fragments thereof used in the therapeutic methods of the present invention may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution.

A strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain.

Polyethylene glycol (PEG) has been widely used as a drug carrier, given its high degree of biocompatibility and ease of modification. Attachment to various drugs, proteins, and liposomes has been shown to improve residence time and decrease toxicity. PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications.

Those of skill in the art are aware of PEGylation techniques for the effective modification of drugs. For example, drug delivery polymers that consist of alternating polymers of PEG and tri-functional monomers such as lysine have been used by VectraMed (Plainsboro, N.J.). The PEG chains (typically 2000 daltons or less) are linked to the a- and e-amino groups of lysine through stable urethane linkages. Such copolymers retain the desirable properties of PEG, while providing reactive pendent groups (the carboxylic acid groups of lysine) at strictly controlled and predetermined intervals along the polymer chain. The reactive pendent groups can be used for derivatization, cross-linking, or conjugation with other molecules. These polymers are useful in producing stable, long-circulating pro-drugs by varying the molecular weight of the polymer, the molecular weight of the PEG segments, and the cleavable linkage between the drug and the polymer. The molecular weight of the PEG segments affects the spacing of the drug/linking group complex and the amount of drug per molecular weight of conjugate (smaller PEG segments provides greater drug loading). In general, increasing the overall molecular weight of the block co-polymer conjugate will increase the circulatory half-life of the conjugate. Nevertheless, the conjugate must either be readily degradable or have a molecular weight below the threshold-limiting glomular filtration (e.g., less than 45 kDa).

In addition, to the polymer backbone being important in maintaining circulatory half-life, and biodistribution, linkers may be used to maintain the therapeutic agent in a pro-drug form until released from the backbone polymer by a specific trigger, typically enzyme activity in the targeted tissue. For example, this type of tissue activated drug delivery is particularly useful where delivery to a specific site of biodistribution is required and the therapeutic agent is released at or near the site of pathology. Linking group libraries for use in activated drug delivery are known to those of skill in the art and may be based on enzyme kinetics, prevalence of active enzyme, and cleavage specificity of the selected disease-specific enzymes (see e.g., technologies of established by VectraMed, Plainsboro, N.J.). Such linkers may be used in modifying the protein or fragment of the protein described herein for therapeutic delivery.

In a preferred embodiment, the feeding disorder with early-onset is selected from the group consisting of Prader-Willi syndrome, and in non-organic failure to thrive disease (NOFTT), resulting from an inability to ingest food, in infants without known organic cause.

In another preferred embodiment, the feeding disorder with early-onset is a Prader-Willi-like syndrome, that is to say a syndrome with a deficit of suckling from birth with an early onset obesity in first years of life.

In another preferred embodiment, the feeding disorder with early-onset is selected from the group consisting of syndromic obesity, premature infants, children with organic hyperinsulinism, children with suckling troubles with or not a Prader-Willi syndrome.

In a preferred embodiment, the agonist according to the invention is given to mammal for treating a feeding disorder with early-onset. More particularly the mammal is a human.

In a particular embodiment, the agonist of the invention may be administrated to a human at any stage of life.

In a preferred embodiment, the agonist according to the invention is given to an infant.

In a particular embodiment, the agonist according to the invention is administrated to an infant and preferably the first three month of life of the infant.

More particularly, the agonist may be administrated chronically from the infant age to the adult age.

In another particular embodiment, the agonist may be administrated to an adult.

In another embodiment, the agonist of the oxytocin receptor is the oxytocin. Preferably, it is a mammal oxytocin. More preferably, it is the human oxytocin.

In another preferred embodiment, the agonist of the invention may be used for the treatment of feeding disorder from birth with suckling deficit.

Nucleic Acids, Vectors, Recombinant Host Cells and Uses Thereof

A second aspect of the invention relates to a nucleic acid molecule encoding the oxytocin or an active fragment thereof for use in the treatment of a feeding disorder with early-onset.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

These nucleic acid molecules may be obtained by conventional methods well known to those skilled in the art, in particular by site-directed mutagenesis of the gene encoding the native protein. Typically, said nucleic acid is a DNA or RNA molecule, which may be included in a suitable vector, such as a plasmid, cosmid, episome, artificial chromosome, phage or viral vector.

So, a further object of the present invention relates to a vector and an expression cassette in which a nucleic acid molecule of the invention is associated with suitable elements for controlling transcription (in particular promoter, enhancer and, optionally, terminator) and, optionally translation, and also the recombinant vectors into which a nucleic acid molecule in accordance with the invention is inserted. These recombinant vectors may, for example, be cloning vectors, or expression vectors.

The terms "vector", "cloning vector" and "expression vector" mean the vehicle by which a DNA or RNA sequence (e.g. a foreign gene) may be introduced into a host cell, so as to transform the host and promote expression (e.g. transcription and translation) of the introduced sequence.

Any expression vector for animal cell may be used, as long as a gene encoding a polypeptide or chimeric derivative of the invention can be inserted and expressed. Examples of suitable vectors include pAGE107, pAGE103, pHSG274, pKCR, pSG1 beta d2-4) and the like.

Other examples of plasmids include replicating plasmids comprising an origin of replication, or integrative plasmids, such as for instance pUC, pcDNA, pBR, and the like.

Other examples of viral vector include adenoviral, retroviral, herpes virus and AAV vectors. Such recombinant viruses may be produced by techniques known in the art, such as by transfecting packaging cells or by transient transfection with helper plasmids or 30 viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. No. 5,882, 877, U.S. Pat. No. 6,013,516, U.S. Pat. No. 4,861,719, U.S. Pat. No. 5,278,056 and WO 94/19478.

Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

The invention also includes gene delivery systems comprising a nucleic acid molecule of the invention, which can be used in gene therapy in vivo or ex vivo. This includes for instance viral transfer vectors such as those derived from retrovirus, adenovirus, adeno associated virus, lentivirus, which are conventionally used in gene therapy. This also includes gene delivery systems comprising a nucleic acid molecule of the invention and a non-viral gene delivery vehicle. Examples of non viral gene delivery vehicles include liposomes and polymers such as polyethylenimines, cyclodextrins, histidine/lysine (HK) polymers, etc.

Another object of the invention is also a prokaryotic or eukaryotic host cell genetically transformed with at least one nucleic acid molecule according to the invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed".

Preferably, for expressing and producing the proteins, and in particular the oxytocin, eukaryotic cells, in particular mammalian cells, and more particularly human cells, will be chosen.

Typically, cell lines such as CHO, BHK-21, COS-7, C127, PER.C6 or HEK293 25 could be used, for their ability to process to the right post-translational modifications of the derivatives.

The construction of expression vectors in accordance with the invention, the transformation of the host cells can be carried out using conventional molecular biology techniques. The V-ATPase c-subunit derivatives of the invention, can, for example, be 30 obtained by culturing genetically transformed cells in accordance with the invention and recovering the derivative expressed by said cell, from the culture. They may then, if necessary, be purified by conventional procedures, known in themselves to those skilled in the art, for example by fractionated precipitation, in particular ammonium sulphate precipitation, electrophoresis, gel filtration, affinity chromatography, etc.

In particular, conventional methods for preparing and purifying recombinant proteins may be used for producing the proteins in accordance with the invention.

Pharmaceutical Compositions

A third object of this invention is a pharmaceutical composition which includes a therapeutically effective amount of at least the agonist according to the invention, along with at least one pharmaceutically acceptable excipient. Alternatively, the pharmaceutical composition of the invention may contain a therapeutically effective amount of a nucleic acid according to the invention or a plasmid or a vector that contains at least one nucleic acid sequence that codes for the oxytocin of the invention, along with at least one adjuvant and/or a pharmaceutically acceptable excipient. Said vector may be used in gene therapy.

By a "therapeutically effective amount" is meant a sufficient amount of the chimeric derivative of the invention to treat a disease associated with retinal degenerative disorder at a reasonable benefit/risk ratio applicable to any medical treatment.

As used herein, the terms "treating" or "treatment", denotes reversing, alleviating, inhibiting the progress of, or preventing the disorder or condition to which such term applies, or one or more symptoms of such a disorder or condition.

According to the invention, the term "patient" or "individual" to be treated is intended for a human or non-human mammal (such as a rodent (mouse, rat), a feline, a canine, or a primate). Preferably, the subject is a human. More preferably, the subject is an infant. Even more preferably, the infant is in the first three months of the life.

It will be understood that the total daily dosage of the agonist and compositions of the present invention will be decided by the attending physician within the scope of sound medical judgment. The specific therapeutically effective dose level for any particular patient will depend upon a variety of factors including the disorder being treated and the severity of the disorder; activity of the specific agonist employed; the specific composition employed, the age, body weight, general health, sex and diet of the patient; the time of administration, route of administration, and rate of excretion of the specific agonist employed; the duration of the treatment; drugs used in combination or coincidental with the specific polypeptide employed; and like factors well known in the medical arts. For example, it is well within the skill of the art to start doses of the agonist at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The therapeutically effective amount of the active product of the invention that should be administered, as well as the dosage for the treatment of a pathological condition with the proteins and/or pharmaceutical compositions of the invention, will depend on numerous factors, including the age and condition of the patient, the severity of the disturbance or disorder, the method and frequency of administration and the particular peptide to be used.

The presentation of the pharmaceutical compositions that contain the agonist of the invention may be in any form that is suitable for administration, e.g., solid, liquid or semi-solid, such as creams, ointments, gels or solutions, and these compositions may be administered by any suitable means, for example, orally, parenterally, inhalation or topically, so they will include the pharmaceutically acceptable excipients necessary to make up the desired form of administration. A review of the different pharmaceutical forms for administering medicines and of the excipients necessary for obtaining same may be found, for example, in the "Tratado de Farmacia Gal nica" (Treatise on Galenic Pharmacy), C. Faul i Trillo, 1993, Luz n 5, S.A. Ediciones, Madrid.

In the pharmaceutical compositions of the present invention for oral, sublingual, subcutaneous, intramuscular, intravenous, transdermal, local, pulmonary, eye drop, intraocular, intranasal or rectal administration, the active principle, alone or in combination with another active principle, can be administered in a unit administration form, as a mixture with conventional pharmaceutical supports, to animals and human beings. Suitable unit administration forms comprise oralroute forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms, intraocular and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising agonist of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The peptides according to the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The protein of the invention may be formulated as a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the agonist of the invention formulated for parenteral administration, such as intravenous or intramuscular injection, other pharmaceutically acceptable forms include, e.g. tablets or other solids for oral administration; liposomal formulations; time release capsules; and any other form currently used.

As previously mentioned, the peptides according to the invention could form part of a combined therapy for the purpose of more effectively stopping an feeding disorder with early-onset. In this case, the invention provides a pharmaceutical composition that includes at least one peptide of the invention; along with another or other compound(s) against of a feeding disorder with early-onset.

An additional object of this invention relates to the agonist of the invention for the treatment of a feeding disorder with early-onset in a patient including but not limited to Prader-Willi syndrome, and in non-organic failure to thrive disease (NOFTT), resulting from an inability to ingest food, in infants without known organic cause.

Moreover, the agonist of the invention may be used for the treatment of behaviour troubles related to impaired social functions observed during childhood and in adult patients with Prader-Willi syndrome or Prader-Willi-like syndrome.

In addition, the invention provides a method for the treatment of an feeding disorder with early-onset in mammals which consists of administering to said mammal suffering from said pathological disease a therapeutically effective amount of at least one agonist of the invention, preferably in the form of a pharmaceutical composition that contains it.

The invention will be further illustrated by the following figures and examples. However, these examples and figures should not be interpreted in any way as limiting the scope of the present invention.

FIGURES

FIG. 1: Targeted Disruption of the Magel2 Gene (A) Maps of the Magel2 wild type, the targeting construct and of the resulting mutant alleles, indicating the replacement of 3.397 kb region including the Magel2 promoter region and part of the Magel2 gene by a LoxP-Pgkl-hygromycin-LoxP cassette (hygro) placed in the opposite transcriptional orientation and introducing new EcoRV sites. The black box represents the Magel2 gene comprised by a single exon, the open box and the two open circles represent the hygromycin resistance gene under the control of the Pgkl promoter, surrounded by the two LoxP sequences (LoxP-hygro-LoxP). The hygromycin resistance gene was secondary removed by expressing the Cre recombinase in ES cells clones, generating the Magel2-null excised allele. The probe used to identify homologous recombination in ES cells by Southern blot analysis is indicated as probe 1.

(B) Southern blot analysis of EcoRV-digested genomic DNA derived from hygromycin-resistant ES cell clones, allowing detection of both mutated (4.5 kb) and wild type (12.8 kb) Magel2 alleles.

(C) PCR analysis of ES cell clones electroporated with a Cre recombinase expressing vector. Deletion of the hygromycin resistance gene detected by the amplification of a 376 bp product is shown in the upper panel (the primers used for the PCR are represented by the two arrows surrounding the hygromycin cassette). It should be noted that the wild type allele cannot be detected as the fragment amplified is too long. A control PCR amplifying a Needin genomic fragment is shown in the lower panel.

(D) Needin and Magel2 in situ hybridization on transverse serial sections through the diencephalon region of E12.5 WT and Magel2 KO mouse embryos. III, third ventricule; hp, hypothalamus region; lv, lateral ventricule; me, median eminence; vt, ventral thalamus; zi, zona intrathalamica. Scale bar: 185 µm.

Figure 2:
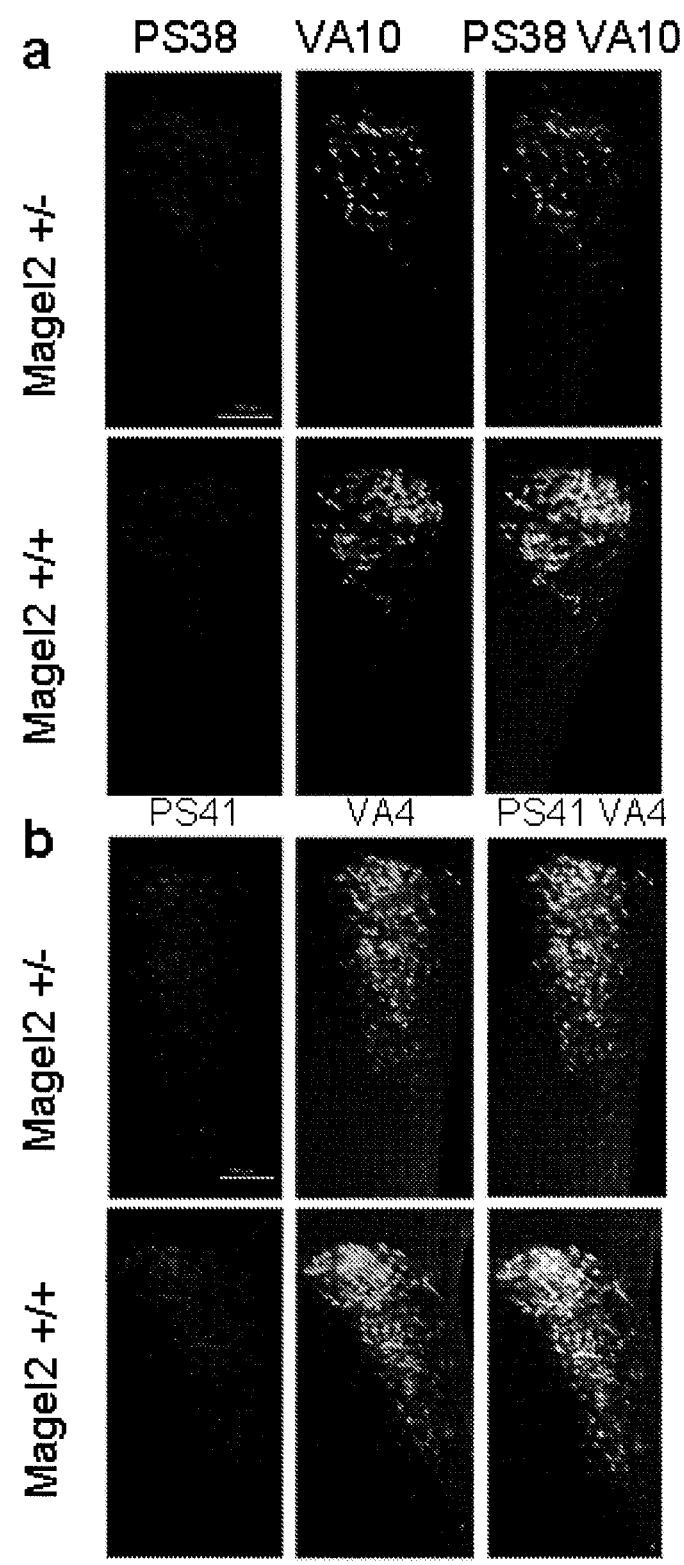

FIG. 2: Impairment in OT but not AVP maturation process in the Magel2 KO PVN. On hypothalamic vibratome sections (100 µm) covering the entire PVN of Magel2 KO (n=7) and wild type (n=5) newborns, we performed a co-immunolabelling using PS-38 and VA-10 antibodies to reveal respectively OT-prohormone and OT-peptide intermediates (a). Similar experiment was done using PS-41 and VA-4 antibodies to reveal respectively AVP-prohormone and AVP-peptide intermediates on PVN of Magel2 KO (n=6) and wild type (n=6) newborns (b).

In Magel2 KO PVN, compared to wild type PVN, we did observe an accumulation of intermediate OT forms (a) but not of intermediate AVP forms (b).

Figure 3:
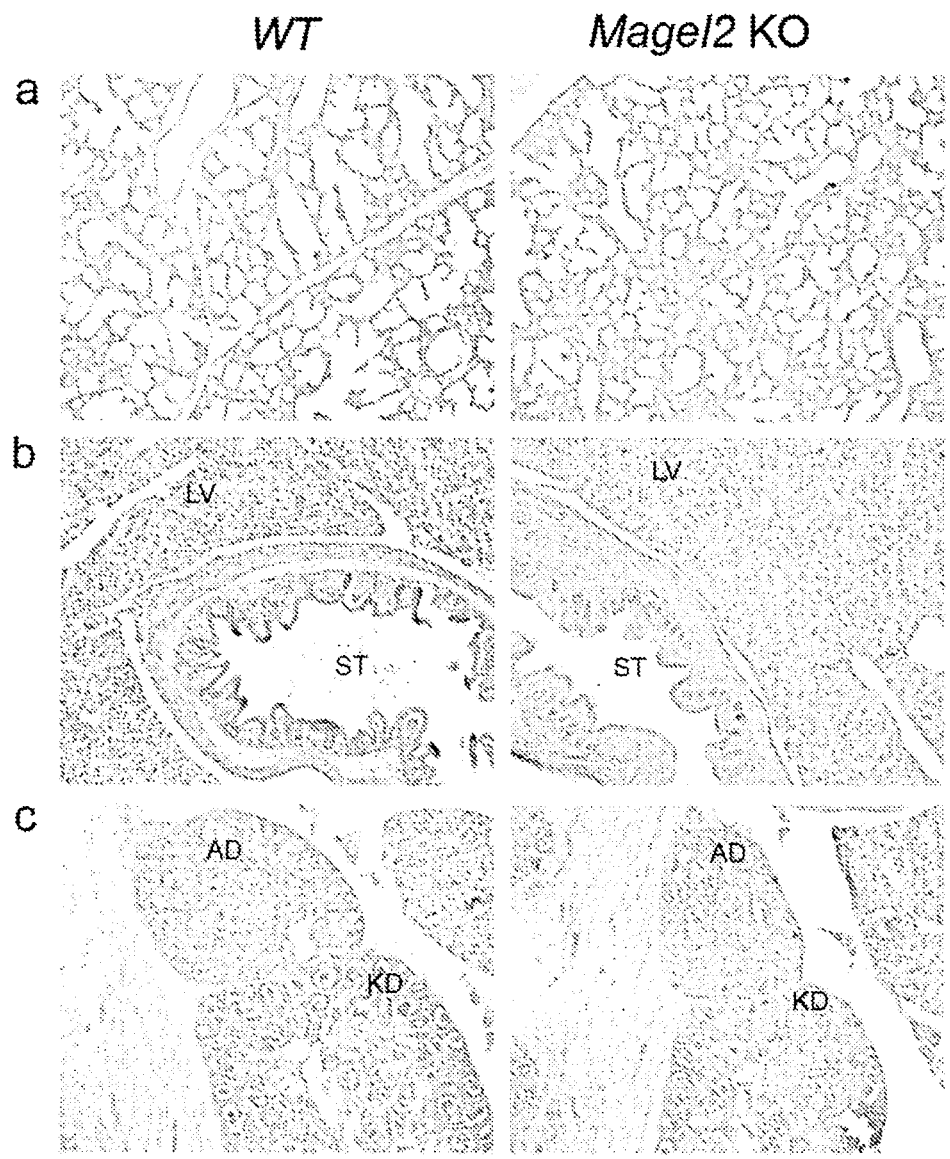

FIG. 3: Normal visceral anatomy of Magel2 KO P1 neonates.

To determine whether internal anatomy was normal, newborns were dissected at P1, body sections were stained with haematoxylin and eosin and visualized by light microscopy. Hematoxylin and eosin staining on sagital sections of P1 wild type (WT) and Magel2 KO neonates. a: lung; b: liver (LV) and stomach (ST); c: kidney (KD) and adrenal gland (AG). Normal anatomy of the lung, the liver, the kidney, the adrenal glands and the heart was observed.

Figure 4:
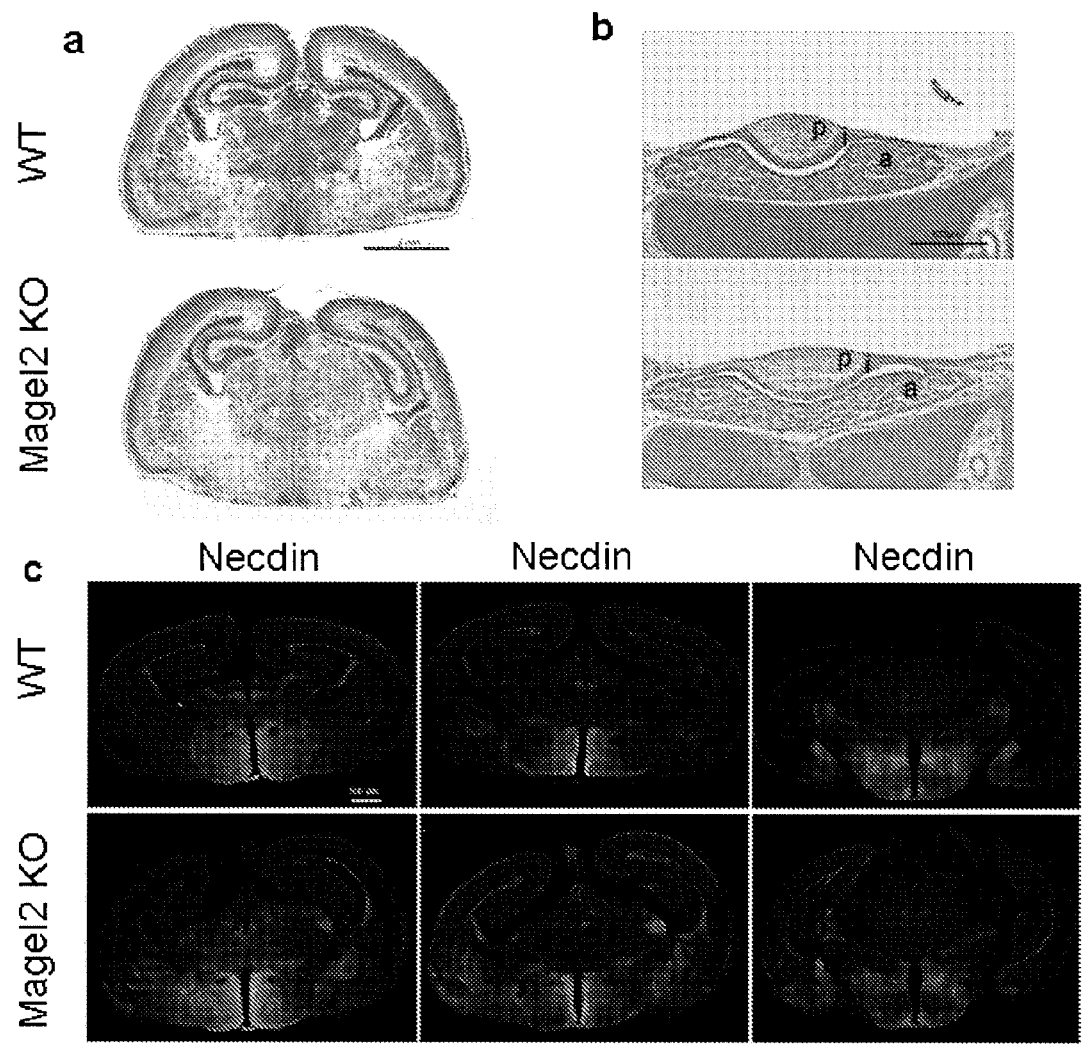

FIG. 4: Brain anatomy of Magel2 mutant neonates.

(a) Niss1 blue staining on coronal brain sections of P0 wild type (WT) and Magel2 KO neonates showing a similar morphology in wild type and mutant neonates. Scale bar: 2 mm.

(b) Hematoxylin and eosin staining on coronal sections of wild type (WT) and Magel2 KO P0 neonates at the level of the pituitary gland. Their structure and size are identical. a, i and p: anterior, intermediate and posterior lobes of the pituitary gland. Scale bar: 100 µm.

(c) Needin immunolabelling on coronal brain sections of wild type (WT) and Magel2 KO P0 embryos, at three different levels of hypothalamus. Needin immunolabelling is similar in both genotypes suggesting that the lack of Magel2 does not modify the set up of hypothalamic nuclei. Scale bar: 300 µm.

Figure 5:
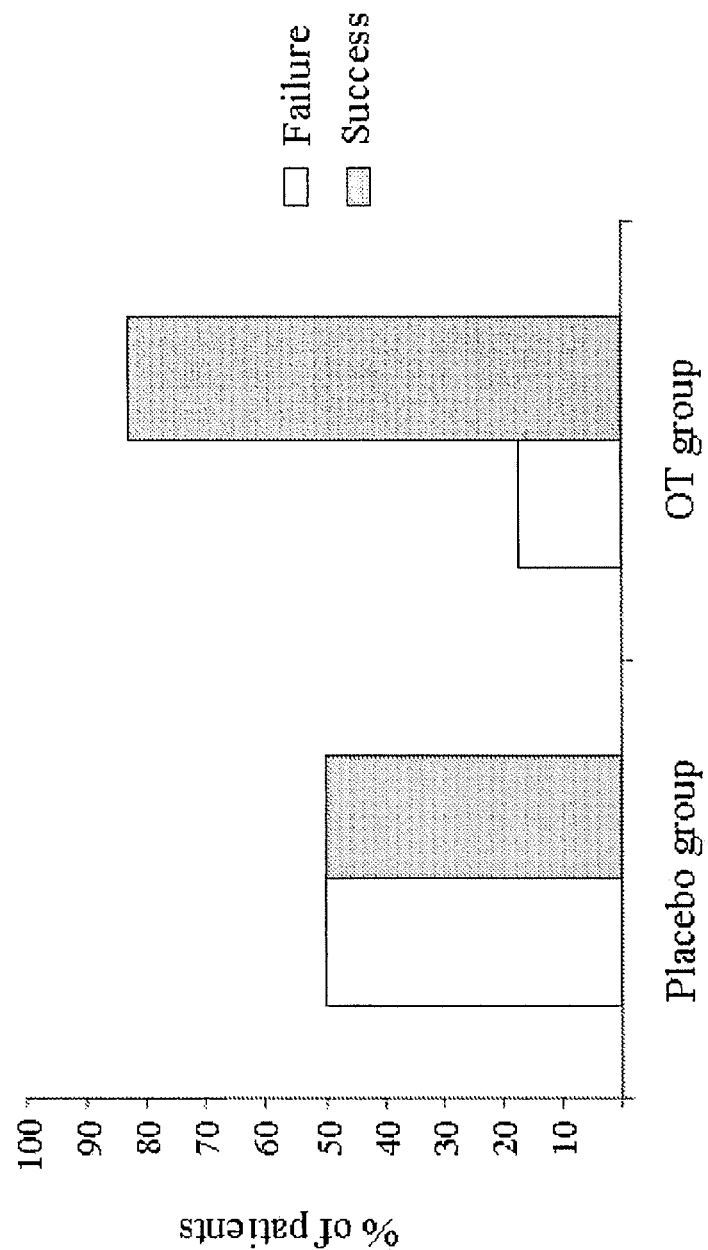

FIG. 5: Percentage of patients in the placebo group in the OT group who failed (white bar) or passed (grey bar) the Sally and Ann test.

TABLE 1

Suckling test

| Genotype of newborns | Suckling activity | | | |
|---|---|---|---|---|
| | Absent | Weak | Strong | TOTAL |
| *WT | 0 | 7 | 6 | 13 |
| *KO | 6 | 2 | 1 | 9 |
| °WT | 1 | 2 | 27 | 30 |
| °KO | 6 | 10 | 6 | 22 |

Suckling activity is considered as: a) absent if there is no attachment to the nipple (scored 0), b) weak if the latency for attachment is over 3 min and suckling activity itself is null or weak and not maintained (scored 1), or c) strong if the latency for attachment is less than 3 min and suckling activity itself is strong (scored 2).

*Pups tested are issued from three litters, about 2-3 hours old. Pups had no milk in their stomach before the test. There is a significant difference in the activity of mutants and controls (Wilcoxon-Mann-Whitney test, $P<0.005$).

° Pups tested are issued from seven litters, between 4 to 8 hours old. Majority of wild type mice had milk in their stomach but mutant had an empty stomach. There is a significant difference in the activity of mutants and controls (Wilcoxon-Mann-Whitney test, $P<0.5c-004$).

TABLE 2

Neuropeptide contents in hypothalamus and pituitary gland of Magel2 mutant and wild type newborns.

| | Hypothalamus P0 (ng/hypothalamus) | | | Pituitary Gland P0 (ng/pituitary) | | |
|---|---|---|---|---|---|---|
| | WT(n = 14) M (Q1, Q3) | KO(n = 14) M(Q1, Q3) | P value | WT(n = 11) M (Q1, Q3) | KO(n = 11) M(Q1, Q3) | P value |
| OT | 4.2 (3.5, 5.7) | 2.7 (2.2, 3.1) | $P<0.005$ | 2.1 (1.9, 2.2) | 2.0(1.8, 2.4) | N.S |
| AVP | 8.4 (8.0, 9.2) | 6.8 (6.4, 7.2) | $P<0.001$ | 6.4 (5.8, 7.0) | 7.2(6.4, 9.2) | N.S |
| OX A | 10.1(9.6, 11.2) | 7.9 (7.5, 9.2) | $P<0.001$ | N.D | N.D | |
| ACTH | 8.6 (8.5, 9.0) | 9.1 (8.0, 9.4) | N.S. | 9.5(8.8, 12.2) | 8.7(8.4, 9.6) | N.S |
| AGRP | 4.8 (3.6, 6) | 5.5 (4.4, 7.2) | $P<0.05$ | N.D | N.D | |
| α-MSH | 5 (3.7, 6.1) | 5.6 (5.0, 6.5) | N.S. | N.D | N.D | |

Results from Elisa tests in order to compare, between mutant and wild type newborns (at P0), the quantity of several neuropeptides produce in hypothalamus or pituitary gland. Values are indicated as: Median (Quartile1, Quartile3)<.

EXAMPLE

Example 1

Mouse Model

Ethics Statement

All breedings and experiments were carried out in keeping with the European guidelines for the care and use of laboratory animals (Council Directive 86/6009/EEC).

Mouse Magel2 KO Line Generation.

Two fragments containing genomic sequences 5' and 3' to the Magel2 region to be deleted were amplified by PCR from 129/SvPas DNA and further verified by sequencing. The 2.651 kb XhoI and 3.062 kb NotI fragments, localised respectively 372 and 3062 bp 5' and 3' to the transcriptional initiation site of the NT_039428.7 Magel2 mRNA (an intronless gene), were inserted on each side of a LoxP-pgkl-hygromycin-LoxP cassette subcloned into a pBluescript II-SK vector (Stratagene). ES (129Sv genetic background) were electroporated and 240 ES cells resistant to hygromycin were screened for homologous recombination and monoinsertion events by Southern blot analysis. Selected clones were electroporated with a Cre recombinase expressing vector. Seven ES cells clones carrying an allele in which the hygromycin resistance gene was deleted were selected by PCR, generating a 376 bp PCR product. Two clones were injected into C57BL/6J blastocysts. Chimeric animals obtained from one of these two clones allowed the transmission of the mutant Magel2 allele detected by PCR in agouti pups, using the same primers as those used to detect the deletion of the hygromycin resistance gene. Mice genotyping was performed by PCR on genomic DNA prepared from tail or placenta biopsies, using the same primers. The Magel2-KO colony was maintained in INMED animal facility (Marseilles).

Neonates Suckling Behaviour.

This test was performed as previously described (Dragatsis, I., et Al., 2004). Briefly, 2-6 h after delivering their newborns, females were anesthetized with 0.1% Rompun Xylasine/10 mg/ml Ketamine Imalgene (0.1 ml/10 g of tissue) and laid down on their back, on a heated surgical pad (37° C.). Newborns were individually tested for their capacity to find and grab to one of their mother's nipple and to suck milk efficiently. Scores are described in Table 1.

In Situ Hybridization and Immunohistochemistry.

Tissues from whole embryos (E12.5) or P0 brains were dissected, fixed and treated as previously described (Andrieu, D., et al., 2003; Muscatelli, F., et al., 2000). 14 µm sagittal or coronal frozen sections were collected. For Magel2 in situ hybridization (ISH) analyses, sections were treated and hybridized with a Magel2 antisense digoxigenin-labeled riboprobe (nucleotides 3366-4053; XM_622091), at 70° C. in 50% formamide, as described previously (Andrieu, D., et al., 2003). For double Magel2 and Needin ISH analyses, sections were hybridized with Magel2 antisense digoxigenin and Needin (nucleotides 2130-2420; D76440) fluorescein-labeled riboprobes (Andrieu, D., et al., 2006). Immunohistochemistry (IHC) on cryosections was performed as previously described (Andrieu, D., et al., 2006). A polyclonal rabbit anti-Needin (#07-565, Upstate; 1/500) was used and immunolabeling was detected with the goat anti-rabbit Alexa Fluor 488 (Molecular Probes, Invitrogen; 1/500) as secondary antibody. Images were acquired with an Axiocam MRm digital camera (Zeiss) on an Axioplan2 Imaging microscope (Zeiss) with an Apotome module (Zeiss), using AxioVision 4.4.1.0 software (Zeiss). Images were assembled with the Adobe Photoshop CS2 software.

Counting Oxytocin, Vasopressin and Prepro-Orexin Neurons in P0 Brains. For oxytocin and vasopressin neurons counting, P0 brains (2-3 hours after birth) were dissected, fixed in AntigenFix (Diapath, Ref P0014) medium O.N. and included in agar 4%. 100 µm vibratome coronal sections were collected from the anterior commissure to the posterior extremity of the hypothalamus. For oxytocin, initially we used a polyclonal anti-oxytocin (OT), which specifically recognizes unidentified forms of OT (a gift from G. Tramu, Muscatelli, F., et al., 2000). Then, we performed co-immunolabelling using a mouse monoclonal antibody highly specific against the mouse neurophysin associated to OT(PS38) and a polyclonal antibody which recognizes the intermediate forms of OT(VA10) (Ben-Barak, Y., et Al., 1985; Altstein, M., at Al., 1987). For vasopressin, we performed co-immunolabelling using a mouse monoclonal antibody highly specific against the mouse neurophysin associated to AVP (PS41) and a polyclonal antibody which recognizes the intermediate forms of AVP (VA4) (Ben-Barak, Y., et Al., 1985; Altstein, M., at Al., 1987). PS38, PS41, VA10 and VA4 are a gift from Pr. H. Gainer.

For prepro-orexin neurons counting, P0 brains were treated as described in immunohistochemistry. 14 μm coronal sections were made with a cryostat and thaw-mounted onto sets of 5 slides, each slide containing rostro-caudal series of sections taken at 70 μm intervals. Sections were collected in the same region as above, which represented a mean of 24 sections. Individual set of slides for each P0 brains were stained with polyclonal rabbit anti-prepro-orexin (#AB3096, Chemicon; 1/250). Immunolabeling was detected with the following secondary antibodies: goat anti-rabbit Alexa Fluor 488 or Alexa Fluor 555 (Molecular Probes, Invitrogen; 1/500), goat anti-mouse Alexa Fluor 488 or Alexa Fluor 555 (Molecular Probes, Invitrogen; 1/500). Slides were mounted in Vectashield mounting medium with DAPI (Vector Laboratories, Inc).

Images were acquired using a confocal microscope (Zeiss, LSM510), z stack of 6 μm were performed for each image. Quantifications were performed with the image analysis software eCELLence (Glance Vision Technologies Sri). All positive neurons were counted on each section in order to count all positive neurons in the entire PVN (OT and AVP) or in the lateral hypothalamus (prepro-orexin).

Enzymes-Linked Immunoassay Analyses.

Enzyme-linked immunoassays analyses were performed to quantify levels of neuropeptides in P0 hypothalamus and hypophyses. P0 hypothalamus and hypophyses were dissected from 10:00 to 12:00 am (delivery occurring in early morning), before post-natal death affecting a proportion of Magel2-KO neonates occurred (mostly from 12:00 hours after birth to P1). Tissues were sonicated in a protease inhibitor cocktail (Complete Mini, Roche), incubated at 95° C. for 10 min to completely inactivate proteases and kept on ice. The protein concentrations were determined on an aliquot of each sample. Neuropeptides were extracted by addition of HCl and acetic acid to a final concentration of 0.02 M and 0.1 M respectively. Samples were centrifuged at 5500 rpm for 20 min and the supernatants were aliquoted before being stored at −80° C. Concentrations of neuropeptides were determined by enzyme-linked immunoassays (EIAs) using Orexin A, Vasopressin[Arg8], Oxytocin, Agouti-related protein (AGRP), alpha-Melanocyte Stimulating Hormone (alpha-MSH), Adrenocorticotropin Hormone ACTH and corticosterone EIA Kits (Phoenix Pharmaceuticals, Inc) according to the manufacturer's instructions. All samples, for series in which concentrations were to be compared, were extracted and assayed in the same experiment.

Injection of Oxytocin and Vasopressin.

Three to 5 hours after delivery, wild type pups or pups issued from a cross between an heterozygote (+/−) male with wild type females were temporally removed (10 min) from their mother, weighted and given a single s.c. (in the ventral region at the level of floating ribs) injection (20 μl) of isotonic saline or 2 μg oxytocin (Phoenix Pharmaceuticals. Inc., Catalog No. 051-01) dissolved in isotonic saline (20 μl). This dose of OT was used because there is a literature indicating that during the neonatal period these doses are not toxic but can affect a variety of physiological responses in male and female rats and prairie voles as well as neuronal activation in neonates 28-29. Following the same protocol, we injected vasopressin (Phoenix Pharmaceuticals. Inc., Catalog No. 065-07) at different doses. At P2, pups were scarified to be genotyped.

Injection of SSR126768A (Antagonist of the Oxytocin Receptor).

A first cohort of C57B16 wild type newborns were removed from their mothers 1-1h30 after their birth and very rapidly were given a single s.c. injection (20 μl) of vehicle control (0.2% ethanol in distilled water) or 3 μg (in 20 μl of 0.2% ethanol in distilled water) of SSR126768A (OTA). A first cohort of C57B16 wild type newborns were injected 12-24 hours after birth. The dose of OTA used was based on previous publications (Serradeil-Le Gal, C., et al., 2004).

We chose to use the Oxytocin antagonist SSR126768A (a gift from C. Serradeil-Le Gal, Sanofi-Synthélabo Recherche, Toulouse, France) because it was already well characterized. It was shown to have a high affinity for OTR in different species, including mouse, and a high selectivity. It has been used at 1, 3 or 10 μg/g in rats (Serradeil-Le Gal, C., et al., 2004) without inducing lethality or any strong secondary effect. Furthermore, at least on uterus, SSR126768A showed a rapid onset of action and a long duration effect (24 h hours after administration with a dose as low as 3 μg/g) (Serradeil-Le Gal, C., et al., 2004).

Statistical Analyses.

Taking in account the size of the sample and the normality or absence of normality of the distribution of the different values, we used appropriate statistical tools. Nonparametric statistical tools (Sigmastat software) or exact statistical tools (StatXact software) were used when it was necessary. All tests are two-tailed tests. In the results, values are indicated as following: (Q2 (Q1, Q3), n, P value) where Q2 is the median, Q1 is the first quartile and Q3 is the second quartile. The level of significance was set at a P-value less than 0.05).

Results

Neonatal Death of Magel2 Deficient Mice.

To elucidate the physiological role of Magel2, we used gene targeting to generate Magel2-null mice (FIG. 1). Since Magel2 is an imprinted gene with a paternal expression only, mice with a paternally deleted Magel2 allele (m+/p−) are thereafter referred as Magel2 KO mice since they are functionally equivalent to Magel2 null mice. These Magel2 KO mice were compared with wild type mice from the same litter. Using in situ hybridization, we checked that Magel2 transcripts were not detected in Magel2 KO embryos (FIG. 1d).

Depending on the genetic background, Magel2 KO mice were significantly under represented at weaning time, revealing a 51.4% lack of Magel2 KO mice after 5 to 7 backcrosses on C57B16/J genetic background. In the surviving mutants, males and females were equally represented.

During embryogenesis (from E10.5 to E18.5) and in early neonates (2-4 hours old), we observed 50% of Magel2 deficient mice, as expected. However, genotyping of litters at P1, revealed that indeed 58% of Magel2 KO mutants versus 99% of wild type were alive whereas 42% of Magel2 KO mutants versus 1% of wild type (WT: n=1, KO: n=32; CHI2 test, P<0.001) were dead during the first day after birth.

Feeding Deficiency in Magel2 Mutants Pups: The Cause of Neonatal Death.

Newborns Magel2 mutants displayed normal proportions of head and body size, in addition to normal pink-colored skin, indicating proper circulatory and respiratory functions.

Apparently, the hearts of mutant neonates beat normally. All organs were present in the KO neonates and similar in-onset to those of wild type littermates as confirmed by a histological analysis (FIG. 3).

However, in a population of 26 litters (104 WT, 104 KO) analysed 3 to 8 hours after birth, 56% (58/104) of Magel2 KO newborns had no milk in their stomachs compared to 16% (17/104) of the controls (CHI2=116, P<0.0005). Then, about 12 hours after birth, we measured the level of glycaemia of Magel2 KO surviving newborns (25% were dead) in order to have a quantitative value of the energetic metabolism. We observed a 30% hypoglycaemia in mutant compared to wild type neonates (WT: 55 mg/dl (46, 65), n=42; KO: 39 mg/dl (28, 52.5), n=35; Wilcoxon-Mann-Whitney test, P<0.001). These data revealed a problem of feeding in Magel2 KO newborns. Indeed, we observed that in 10 litters, 58% (19/39) Magel2 KO individuals died between P0 and P1 versus 5% (2/39) wild type mice and, post mortem analysis revealed that none of them had milk in their stomach.

In parallel, we followed the growth of surviving mutants compared to wild type newborns. First, between P0 and P3, we observed a 43% significant reduction in the weight gain of Magel2 KO compared to wild type individuals (4 litters, WT: 0.52 g (0.27, 0.73), n=16; KO: 0.22 g (0.18, 0.31), n=13; Wilcoxon-Mann-Whitney test with stratum=litter, P<0.005); but this difference in weight gain disappeared between P3 and P4 (WT: 0.33 g (0.34, 0.35), n=16; KO: 0.34 g (0.34, 0.39), n=13, N.S.).

Taken together, these data suggest that in the absence of Magel2, the initiation of feeding process after birth is altered, leading to an early death of 50% of mutants.

Feeding Behaviour in Magel2 KO Pups: The Onset of Suckling Activity is Disturbed.

As a newborn, one crucial step to survive is to find food. Indeed, mouse neonates have to find their mother's nipples and by themselves suckle. This step involves: an awaked state, an olfactory or tactile functional system to locate the mother's nipples, a rooting reflex, a rhythmic suckling reflex and swallowing (Hongo, T., et Al., 2000). Thus, several sensory and motor systems involving different brain structures and muscles are implicated (Delaney, A. L. & Arvedson, J. C, 2008).

Soon after birth, Magel2 KO pups do not appear hypotonic and react with similar movements as observed in controls, notably when they are placed on their back. During the first postnatal day, control and mutant pups exhibited a similar rooting reflex. Furthermore Magel2 KO newborns could open and close their mouth normally. All these observations are in agreement with a normal motor activity necessary for suckling in Magel2 mutants.

Then, we performed a suckling test, recording the attachment of the newborn to the mother's nipple (Dragatsis, 1., et Al, 2004). We observed a significant difference in suckling activity (Wilcoxon-Mann-Whitney test, P<0.005) between wild type and Magel2 KO newborns issued from 10 litters (Table 1): 39% (12 of 31) of Magel2 mutant versus 2% (1/43) of wild type animals had no suckling activity, 39% (12/31) of Magel2 mutant versus 21% (9/43) of wild type animals had a weak suckling activity and only 22% (7/31) of Magel2 mutant versus 77% (33/43) of wild type animals have a strong activity. Altogether, these data suggested that at birth Magel2 KO mice had defects in the process initializing the suckling stimulation leading 50% of these newborns to an impaired feeding and death. 50% of these mutant neonates were able, apparently with some difficulties, to initiate the suckling process and survive.

Neuroendocrine Function During the Early Postnatal Period in Magel2 KO.

The absence of obvious structural modifications in brain anatomy and in hypothalamus of mutant newborns (FIG. 4) does not exclude a functional alteration of this structure. The production of neuropeptides and hormones might be modified, in particular those which are known to play an important role at birth.

Circulating glucocorticoids are thought to play an important role in the adaptation of the neonate to the extra uterine life (Lesage, J., et Al., 1996; Girard, J. et Al., 1992), in particular in the activation of liver or gastrointestinal enzymes to regulate energy homeostasis (Boksa, P., 1997). Just after birth, a sex independent abrupt rise in plasma AdrenoCorticoTropin Hormone (ACTH) (10 min after birth) has been previously described, followed by an increase in plasma and adrenal corticosterone levels (one hour after birth) (Lesage, J., et Al., 1996). We then used enzyme immunoassay (EIA) tests and compared the level of plasma ACTH, in caesarean-section newborns (E18.5), 10 min after birth, and the level of plasma corticosterone, 60 min after birth, between Magel2 KO and wild type mice. We did not observe any significant difference in the ACTH plasma level (WT: 5.4 ng/ml (4.6, 5.8), n=9; KO: 5.9 ng/ml (5.4, 6.1), n=11; Wilcoxon Mann-Whitney test, N.S.). Similarly, the corticosterone plasma level, one hour after birth, did not differ significantly between both genotypes (WT: 750 ng/ml (650, 1050), n=10; KO: 575 ng/ml (425, 750), n=10; Wilcoxon Mann-Whitney test, N.S.).

Several hypothalamic neuropeptides are also thought to play an important role, during the early postnatal period such as Oxytocin (OT) (Carter, C. S., 2003), Arginine-Vasopressin (AVP) (Zelena, D., et al., 2008; Reymond-Marron, I., at Al., 2006; Liu, X., et Al., 2003), and Orexin-A (OXA) (Dickinson, H., et Al., 2008). Using an EIA approach, the quantity of these mature neuropeptides produced in the hypothalamus and in the hypophysis of Magel2 mutant neonates and their wild type littermates was measured. In the hypothalamus, we observed an average of 36% reduction in the production of OT, a 20% reduction of AVP and a 22% reduction of OXA (Table 2). The levels of ACTH, and alpha-Melanocyte Stimulating Hormone ($\alpha$-MSH) which are two products derived from propiomelanocortin are similar in mutants and wild type newborns (Table 2). In the pituitary gland, the quantity of OT, AVP and ACTH was similar between both genotypes (Table 2). In conclusion, the deficiency in Magel2 expression leads to an impairment of hypothalamic production of at least several mature amidated neuropeptides (OT, AVP, OX-A), the production of OT being the most affected.

Immunohistochemical Analyses of Hypothalamic Neurons Producing OT, AVP and OXA.

Then, we looked at the distribution of hypothalamic neurons expressing these peptides by immunohistochemistry (IHC). Initially, using an anti-OT antibody which is able to recognize uncharacterized forms of OT, we visualised at P0 (3-5 hours after birth) an increased OT immunolabelling, in the PVN of mutant compared to wild type animals (3 mice per group). Since we revealed a 36% decrease in OT mature form in Magel2 KO hypothalamus by EIA, the increased immunolabelling might be due to an accumulation of a not fully OT processed form. In order to discriminate what forms might be accumulated, we then used a couple of antibodies allowing us to specifically stain for 1) OT-associated neurophysin (PS-38) detecting the respective OT prohormone and 2) for the OT peptide intermediates (VA-10) (Ben-Barak, Y., et Al., 1985; Whitnall, M. H., et Al., 1985; Altstein, M., et Al., 1987). Using co-immunolabelling (FIG. 2a) followed by confocal microscopy analysis, we quantified the number of positive cells for each antibody in the PVN of newborns (3-5 hours after birth). The number of PS-38 positive cells was similar between mutant and wild type animals (WT: 237 (226, 298), n=5; KO: 300 (279, 303), n=7; N.S.). But, on the same sections, the number of VA-10 positive cells was significantly higher in the PVN of Magel2 KO compared to wild type PVN (WT: 259 (239, 309), n=5; KO: 442 (387, 469), n=7; Wilcoxon-Mann-Whitney P<0.005). Since the VA-10 antibody recognizes specifically intermediate OT forms (mainly OT-G), we conclude to an increase of 1.7 fold in the accumulation of intermediate OT forms in the Magel2 KO PVN compared to wild type PVN.

Similarly to this study, we performed a co-immunolabelling on PVN sections using antibodies specifically raised against the AVP-associated neurophysin (PS-41) and the AVP-peptide intermediates (VA4) (Ben-Barak, Y., et Al., 1985; Whitnall, M. H., et Al., 1985; Altstein, M., et Al., 1987). A confocal analysis (FIG. 2b) and quantification of PS-41 (KO: 375 (304, 386), n=6; WT: 362 (314, 387), n=6; N.S.) and VA4 (KO: 379 (360, 391), n=6; WT: 407 (390, 417), n=6; N.S.) positive neurons in mutant and wild type PVN revealed no significant difference between both genotypes. Thus, in Magel2 KO PVN, we did not observe an accumulation of intermediate AVP forms as we observed for OT.

Finally, we also used an antibody that recognizes specifically the prepro-orexin, the initial unprocessed form of OXA. We observed a similar immunolabelling and we counted the same number of prepro-orexin-expressing neurons in the lateral hypothalamus of mutant (258 (253, 269), n=5) and wild type (264 (235, 266), n=5) animals analysed at P0 (data not shown).

In conclusion, these results suggest that the reduced quantity of amidated OT detected in Magel2 KO hypothalami in neonates might be the consequence of an impairment in the transformation of OT intermediate forms to amidated OT, leading to an accumulation of these intermediate forms. This defect is not observed for AVP.

Injection of an Oxytocin Receptor Antagonist Prevents Feeding in Wild Type Neonates and Induces Postnatal Lethality.

Taking in account all the previous data, we hypothesized that OT deficiency might be responsible for the Magel2 KO phenotype at birth. Consequently, we decided to inject the SSR 126768A compound, a specific OT antagonist (OTA) with high affinity with the OT receptor (Serradeil-Le Gal, C., et al., 2004). We proceeded to a single injection of 3 µg (20 µl) in 68 wild-type C57B16/J newborns (9 litters), 1 to 1.5 hour after birth. In parallel, in the same conditions, we injected the vehicle (200) in 48 wild-type C57B16/J newborns (7 litters). Then, 12 (+/−3) hours after the injection time, we observed than 54% (37/68) of newborns injected with OTA had no milk in their stomach versus 4% (2/48) of newborns injected with vehicle. At P1 (24-36 h old), we observed than 48% (33/68) of newborns injected with OTA were dead versus 4% (2/48) of newborns injected with vehicle control. We concluded that the SSR 126768A OTA had a significant effect in wild type C57B1/6J newborns, preventing half of them to feed correctly and leading to lethality at P1. However, when we injected the SSR 126768A OTA (3 µg in 20 µl) in 42 wild-type pups, 12-24 hours after birth, all of them survived 48 hours later and appeared healthy. Thus, the SSR 126768A OTA at a dose of 3 µg appeared to have a specific effect, preventing the feeding process and leading to death, only when it was injected in a specific window of time after birth, before the suckling activity was initiated. This phenotype simulates the Magel2 KO feeding phenotype at birth.

The Suckling Initiation Deficit Phenotype and the Lethality Resulting from a Lack of Magel2 can be Rescued by Injection of Oxytocin.

The results obtained with the injection of SSR 126768A OTA let us think that we might restore a normal feeding behaviour in Magel2 KO newborns with an OT injection just after birth. Early neonatal manipulation of OT was reported in the literature without alterations of the postnatal development (Cushing, B. S., et Al., 2003; Yamamoto, Y., et al., 2004; Saito, O., et Al., 2007). Initially, 28 wild type newborns were injected with an isotonic saline (20 µl) and 4 of them died at P1. Another cohort of 28 wild type newborns, at the same are observed on hypothalamic nuclei one hour after the injection (Cushing, B. S., et Al., 2003; Yamamoto, Y., et al., 2004). We then decided to inject 2 µg of OT in Magel2 KO and wild type newborns, 3 to 5 hours after birth, the time when wild type newborns started to suckle but not the mutant neonates. In a first step, using two cohorts of wild type pups (n=28), we checked that a subcutaneously (s.c.) injection of isotonic saline (20 µl NaCl 0.9%) and a s.c. injection of oxytocin (2 µg in 20 µl of NaCl 0.9%) solution did not induce lethality. The level of lethality is similar after an injection of saline solution (4/28 dead pups) or oxytocin (3/28 dead pups) and is in the range of lethality normally observed in wild type cohorts. In a second step, ten litters including a total of 37 wild type and 40 Magel2 KO neonates, were injected with an oxytocin solution. At P2, we observed that 95% (35/37) of wild type and 93% (37/40) of Magel2 mutant newborns survived with milk previously detected in their stomach at P1. In parallel, we controlled that the rescue of Magel2 KO neonates was specifically due to the oxytocin injection and not to the injection stress and/or handling of neonates. In a control experiment we performed an s.c. vehicle injection in 33 Magel2 mutant and 37 wild type neonates. At P1 we estimated at 48.5% (16/33) the lethality among Magel2 KO individuals although only 1 (2.7%) wild type pup died. Noticeably the death of these 16 Magel2 mutants is correlated with a lack of milk in the stomach of the carcasses. The high percentage (48.5%) of lethality observed in Magel2 pups but not in wild type pups, both being injected with isotonic saline, is comparable with the lethality observed in non treated Magel2 newborns.

Similar experiments were performed with AVP injections but whatever the dose injected, AVP did not rescue the phenotype of Magel2 deficient neonates.

We conclude that one single injection of OT, in a specific window of time, 3-5 hours after birth, was able to efficiently rescue the death rate due to the feeding deficit observed in Magel2 KO newborns.

Example 2

Administration of Oxytocin in Adult Patients with PWS

Material & Methods

The inventors designed a double-blind randomised, placebo-controlled pilot study (ClinicalTrials.gov Identifier: NCT01038570) to be conducted in a dedicated PWS centre, where patients are regularly admitted for one month and live in a controlled environment. Patients know they have no free access to food but no doubt about the time and the content of meals. For each stay, 16 patients with PWS are admitted and take part in daily planned occupational and physical group activities. They also receive medical care as needed and psychological support. The 24 patients included in this study (16 females, 8 males, median age 28.5 years [18.7 to 43.6], median BMI 43 kg/m2 [19.4 to 67.4]) were stratified on gender and IQ (median IQ=51 [45 to 75]). The diagnosis of PWS was genetically confirmed using the standard DNA methylation test and subsequent molecular analyses showed a classic genotype distribution. Nineteen patients had a deletion (79%), three (12.5%) a UPD, and in two cases (8.5%) the genetic subtype was unknown. Patients as well as parents or caregivers gave their written consent prior to entering the study. Exclusion criteria were an abnormal ECG and other severe cardiovascular problems. Patients were well known to the team. Each pair of patients of the same gender and same IQ range was evaluated the same day. The two patients of the pair received either OT or placebo in a double-blind randomisation. Patients were included in the study over the course of three series of stays.

Each patient received a single intranasal administration of either placebo (saline solution) or OT (Syntocinon®/-Spray, Novartis, Basel, Switzerland) with three puffs per nostril (24 UI). The dose of 24 UI is the most frequently reported in the literature. As the inventors did not succeed in obtaining empty flasks of Syntocinon® from Novartis, the inventors used a different flask and the drug was administered by a nurse from another department of the hospital. This nurse knew neither the patients nor the study.

The behaviour of the patients was carefully monitored, scored daily by the team psychologist, and documented on the case report form for the two days before drug administration, on the half-day following administration (early effects) and over the two days following drug administration (late effects). Both the staff and the rater were unaware of treatment status. There are currently no validated grids that evaluate the specific behavioural features of patients with PWS that they particularly wanted to study, i.e. tendencies towards isolation, sadness, and depression, self-depreciation, self-mutilation, conflicts with others, disruptive behaviour, interest in friendship, interest in love affairs, and trust of others. For this reason, they used an in-house grid developed by the caregivers and based on the routine observation of these patients in this dedicated centre for PWS with recognized expertise (17, 18). The criteria that the staff used to fill in the grid are explained in Table 1. The patients were well known to the team but the mean behavior status was re-evaluated during the first week of admission using the same grid. The behavioural features of the patients were scored as unchanged, moderately changed, or severely changed. For each criterion, a negative score reflected deterioration in the mean behavior status of the patient while a positive score reflected an improvement. Eating behaviour was also scored using three categories: usual, better than usual or worse, based on the analysis of each meal. The following were evaluated: amount of food intake per meal, amount of food requested per meal, duration of meal, and behaviour before/during/after the meal. To evaluate the early effect of OT, we analysed only the first meal after drug administration.

Forty-five minutes after the intranasal administration, three tests evaluating the understanding of social codes were administered, which lasted one hour. Conversely to the behavioural grid, there was no pre-administration evaluation. The Sally and Ann test assesses one's ability to understand simple situations by story-telling and pictures. Cartoons depicting more complex social situations designed for the evaluation of autistic children were also used ("Cartoons", unpublished test). The "Reading the Mind in the Eyes" test (RMET) assesses the ability to read emotions from subtle affective facial expressions, especially in the eyes. A shortened test with 19 images from the 36-item revised version was chosen by the team psychologist. In these three tests, TOM is necessary to understand and analyse the social situations that are presented. Statistical analysis was performed using the Mann-Whiney test, the Wilcoxon test or the chi2 test.

Four patients in the OT group and three in the placebo group were receiving psychotropic medications.

Results

Patients in the OT group displayed significantly increased trust in others (P=0.02), fewer tendencies towards sadness (P=0.02) and less disruptive behaviour (P=0.03) in the two days following intranasal drug administration. They also showed a tendency towards fewer conflicts with peers (P=0.07) on the half-day following intranasal administration. Table 2 shows these results in detail. Of note, there was no difference between the two groups before intranasal administration for any item.

In the group of the 19 patients with deletions (9 in the OT group, 10 in the placebo group), a significant effect of intranasal OT on disruptive behaviour was also found (P=0.04), as well as a trend towards more trust in others (P=0.05) fewer sadness tendencies (P=0.07) and more interest in friendship (P=0.05) (data not shown). The low number of patients with no deletion (n=5) did not allow statistical analysis (data not shown).

The same analysis was performed excluding the seven patients who received psychotropic medications (4 patients in the OT group and 3 in the placebo group) and showed that the OT group had less disruptive behaviour (P=0.04) in the two days following intranasal drug administration (data not shown).

The pre-post difference, which was calculated as "post-administration late effect score" minus "pre-administration score", was significant in the OT group for the disruptive behaviour (P=0.01) and self-mutilation (P=0.047) items, whereas there was no difference in the placebo group (Table 3). There was a trend (P=0.07) towards a different evolution in the pre-post difference between the two groups for the disruptive behaviour item.

No statistical difference was observed in the scores assessing eating behaviour between the two groups. Nevertheless, five patients in the OT group (45%) and one in the placebo group (10%) said that they did not feel hungry and slightly decreased their food intake over the two days following the intranasal administration.

The tests evaluating social skills showed a tendency towards improvement in the OT group (n=12). Eighty-three percent of the patients in this group successfully completed the Sally and Ann test compared with 50% in the placebo group (n=12) (P=0.19, FIG. 1). The same tendency was observed with the Cartoons, with a higher score obtained in the OT group than in the placebo group: 3.75 (1-18) vs. 6 (0-12) (P=0.56). There was no significant difference in the total RMET score between the two groups: 7 (4-9) in the OT group vs. 5.5 (1-11) (P=0.18).

Tolerance of OT was excellent with no effect on electrocardiogram and PSA. No adverse event was observed during the study.

TABLE 1

Criteria used by the staff to fill out the behavioural grid.

| Behavioural items | Scoring criteria |
|---|---|
| Isolation tendencies | playing solitary games, taking walks alone |
| Sadness tendencies | mood state expressed by tears, complaints, frustration, irritation with others |

TABLE 1-continued

Criteria used by the staff to fill out the behavioural grid.

| Behavioural items | Scoring criteria |
|---|---|
| Depressive tendencies | remaining in bed, neglecting self-care, showing little motivation or interest, withdrawn |
| Self-depreciation | belittling self, pointing out own incapacities and failings, expressing low self-value |
| Self-mutilation | mutilations: scratching or scraping off skin, pulling out hair or eyebrows |
| Conflicts with others | opposing others, verbal or physical disputes, other-directed complaints, making threats temper tantrums, sulking, running away, slamming doors, |
| Disruptive behaviour | isolating self in room, breaking things, etc., in response to a conflict or a frustration |
| Interest in friendship | making friends with other patients, taking part in group activities |
| Interest in love affairs | showing interest in having a special relationship with someone of the opposite sex (or not . . . ) participating in group activities, talking with others while |
| Trust in others | taking walks, spontaneously greeting others, introducing self to caregivers or asking for help, etc. |

TABLE 2

Behavioural scores pre- and post-administration of OT in the placebo and OT groups; pre-administration score is the mean of the scores reported on the two days before administration; Early effect is the immediate score recorded the half-day following administration and late effect is the mean of the scores reported on the two days following administration (the immediate score recorded the half-day following administration was excluded).

| Variable | Placebo Group | OT Group | P-value |
|---|---|---|---|
| Isolation tendencies | | | |
| Pre-administration | −0.111 ± 0.296 | −0.083 ± 0.289 | 0.580 |
| Early effect | −0.250 ± 0.452 | −0.083 ± 0.289 | 0.284 |
| Late effect | −0.111 ± 0.217 | 0 ± 0 | 0.070 |
| Sadness tendencies | | | |
| Pre-administration | −0.208 ± 0.276 | −0.194 ± 0.407 | 0.513 |
| Early effect | −0.083 ± 0.289 | −0.083 ± 0.289 | >0.99 |
| Late effect | −0.347 ± 0.379 | −0.083 ± 0.289 | 0.021 |
| Depressive tendencies | | | |
| Pre-administration | −0.028 ± 0.096 | −0.056 ± 0.192 | 0.952 |
| Early effect | 0 ± 0 | 0 ± 0 | >0.99 |
| Late effect | −0.125 ± 0.311 | 0 ± 0 | 0.149 |
| Self-depreciation | | | |
| Pre-administration | −0.028 ± 0.096 | −0.056 ± 0.192 | 0.952 |
| Early effect | 0 ± 0 | −0.083 ± 0.289 | 0.317 |
| Late effect | −0.083 ± 0.289 | 0 ± 0 | 0.317 |
| Self-mutilation | | | |
| Pre-administration | −0.069 ± 0.166 | −0.278 ± 0.468 | 0.271 |
| Early effect | −0.083 ± 0.289 | −0.083 ± 0.289 | >0.99 |
| Late effect | −0.028 ± 0.096 | −0.083 ± 0.195 | 0.482 |
| Conflicts with others | | | |
| Pre-administration | −0.208 ± 0.276 | −0.319 ± 0.359 | 0.467 |
| Early effect | −0.250 ± 0.452 | 0 ± 0 | 0.07 |
| Late effect | −0.125 ± 0.237 | −0.111 ± 0.205 | 0.939 |
| Disruptive behaviour | | | |
| Pre-administration | −0.361 ± 0.354 | −0.431 ± 0.344 | 0.744 |
| Early effect | −0.250 ± 0.452 | −0.167 ± 0.389 | 0.623 |
| Late effect | −0.306 ± 0.382 | −0.042 ± 0.144 | 0.031 |
| Interest in friendship | | | |
| Pre-administration | 0.806 ± 0.324 | 0.875 ± 0.433 | 0.349 |
| Early effect | 0.833 ± 0.389 | 0.917 ± 0.515 | 0.683 |
| Late effect | 0.778 ± 0.410 | 1.028 ± 0.234 | 0.088 |
| Interest in love affairs | | | |
| Pre-administration | 0.847 ± 0.579 | 0.972 ± 0.531 | 0.589 |
| Early effect | 0.833 ± 0.389 | 0.917 ± 0.515 | 0.683 |
| Late effect | 0.847 ± 0.441 | 0.903 ± 0.411 | 0.714 |
| Trust in others | | | |
| Pre-administration | 0.833 ± 0.389 | 0.861 ± 0.332 | 0.929 |
| Early effect | 0.917 ± 0.289 | 0.833 ± 0.389 | 0.546 |
| Late effect | 0.764 ± 0.366 | 1.028 ± 0.096 | 0.023 |

TABLE 3

Pre-post differences in the behavioural scores of the two groups and change comparison between OT treatment and placebo.

| | Placebo group | | | OT group | | | OT vs Placebo |
|---|---|---|---|---|---|---|---|
| Change in behavioural scores | Mean | SD | P-value (Mann Whitney) | Mean | SD | P-value (Mann Whitney) | P-value (Wilcoxon*) |
| Isolation tendencies | −0.000 | 0.402 | 0.723 | 0.083 | 0.289 | 0.317 | 0.404 |
| Sadness tendencies | −0.139 | 0.324 | 0.260 | 0.111 | 0.533 | 0.343 | 0.217 |
| Depressive tendencies | −0.097 | 0.230 | 0.158 | 0.056 | 0.192 | 0.317 | 0.088 |

TABLE 3-continued

Pre-post differences in the behavioural scores of the two groups
and change comparison between OT treatment and placebo.

| Change in behavioural scores | Placebo group | | | OT group | | | OT vs Placebo |
|---|---|---|---|---|---|---|---|
| | Mean | SD | P-value (Mann Whitney) | Mean | SD | P-value (Mann Whitney) | P-value (Wilcoxon*) |
| Self-depreciation | −0.056 | 0.192 | 0.317 | 0.056 | 0.192 | 0.317 | 0.166 |
| Self-mutilation | 0.042 | 0.203 | 0.530 | 0.194 | 0.354 | 0.047 | 0.236 |
| Conflicts with others | 0.083 | 0.314 | 0.735 | 0.208 | 0.498 | 0.150 | 0.532 |
| Disruptive behaviour | 0.056 | 0.457 | 0.812 | 0.389 | 0.385 | 0.011 | 0.070 |
| Interest in friendship | −0.028 | 0.497 | 0.690 | 0.153 | 0.379 | 0.183 | 0.245 |
| Interest in love affair | −0.000 | 0.632 | 1.000 | −0.069 | 0.429 | 0.600 | 0.704 |
| Trust in others | −0.069 | 0.399 | 0.850 | 0.167 | 0.333 | 0.084 | 0.222 |

*Wilcoxon test is based on individual changes.

REFERENCES

Altstein, M., Dudai, Y. & Vogel, Z. Angiotensin-converting enzyme associated with Torpedo california electric organ membranes. J Neurosci Res 18, 333-340 (1987).

Andrieu, D., et al. Expression of the Prader-Willi gene Needin during mouse nervous system development correlates with neuronal differentiation and p75NTR expression. Gene Expr Patterns 3, 761-765 (2003).

Andrieu, D., et al. Sensory defects in Needin deficient mice result from a loss of sensory neurons correlated within an increase of developmental programmed cell death. BMC Dev Biol 6, 56 (2006).

Ben-Barak, Y., Russell, J. T., Whitnall, M. H., Ozato, K. & Gainer, H. Neurophysin in the hypothalamo-neurohypophysial system. 1. Production and characterization of monoclonal antibodies. J Neurosci 5, 81-97 (1985).

Bittel, D. C. and M. G. Butler (2005). "Prader-Willi syndrome: clinical genetics, cytogenetics and molecular biology." Expert Rev Mol Med 7(14): 1-20.

Boksa, P. Early developmental profiles of plasma corticosterone are altered by birth condition in the rat: a comparison of vaginal birth, cesarean section, and cesarean section with added anoxia. Pediatr Res 41, 34-43 (1997).

Carter, C. S. Developmental consequences of oxytocin. Physiol Behav 79, 383-397 (2003).

Cassidy, S. B. and D. J. Driscoll (2009). "Prader-Willi syndrome." Eur J Hum Genet. 17(1): 3-13.

Cushing, B. S., Yamamoto, Y., Hoffman, G. E. & Carter, C. S. Central expression of c-Fos in neonatal male and female prairie voles in response to treatment with oxytocin. Brain Res Dev Brain Res 143, 129-136 (2003).

de Smith, A. J., C. Purmann, et al. (2009). "A deletion of the HBII-85 class of small nucleolar RNAs (snoRNAs) is associated with hyperphagia, obesity and hypogonadism." Hum Mol Genet. 18(17): 3257-65.

Delaney, A. L. & Arvedson, J. C. Development of swallowing and feeding: prenatal through first year of life. Dev Disabil Res Rev 14, 105-117 (2008).

Dickinson, H., Walker, D. W. & Castillo-Melendez, M. Onset of feeding at birth—perinatal development of the hypothalamic mechanisms that induce appetite and feeding in the newborn. Neurosci Lett 436, 1-6 (2008).

Dragatsis, I., Zeitlin, S. & Dietrich, P. Huntingtin-associated protein 1 (Hap 1) mutant mice bypassing the early postnatal lethality are neuroanatomically normal and fertile but display growth retardation. Hum Mol Genet. 13, 3115-3125 (2004).

Girard, J., Ferre, P., Pegorier, J. P. & Duee, P. H. Adaptations of glucose and fatty acid metabolism during perinatal period and suckling-weaning transition. Physiol Rev 72, 507-562 (1992).

Goldstone, A. P. (2004). "Prader-Willi syndrome: advances in genetics, pathophysiology and treatment." Trends Endocrinol Metab 15(1): 12-20.

Hongo, T., Hakuba, A., Shiota, K. & Naruse, I. Suckling dysfunction caused by defects in the olfactory system in genetic arhinencephaly mice. Biol Neonate 78, 293-299 (2000).

Lesage, J., Bernet, F., Montel, V. & Dupouy, J. P. Hypothalamic metabolism of neurotransmitters (serotonin, norepinephrine, dopamine) and NPY, and gonadal and adrenal activities, during the early postnatal period in the rat. Neurochem Res 21, 87-96 (1996).

Liu, X., Tribollet, E., Ogier, R., Barberis, C. & Raggenbass, M. Presence of functional vasopressin receptors in spinal ventral horn neurons of young rats: a morphological and electrophysiological study. Eur J Neurosci 17, 1833-1846 (2003).

Manning Maurice, Stoytcho Stoev, Bice Chini, Thierry Durroux, Bernard Mouillac and Gilles Guillon. Peptide and non-peptide agonists and antagonists for the vasopressin and oxytocin V1a, V1b, V2 and OT receptors: research tools and potential therapeutic agents. Progress in Brain Research, 2008, Vol. 170 ISSN 0079-6123.

Muscatelli, O. D. a. F. (2008). Prader-Willi Syndrome. Obesity. Genomics and Postgenomics. K. C. a. T. Sorensen, Informa Healthcare: 179-193.

Muscatelli, F., et al. Disruption of the mouse needin gene results in hypothalamic and behavioral alterations reminiscent of the human prader-willi syndrome [In Process Citation]. Hum Mol Genet. 9, 3101-3110 (2000).

Pitt Gary R. W., Andrzej R. Batt, Robert M. Haigh, Andrew M. Penson, Peter A. Robson, David P. Rooker, Andre' L. Tartar, Julie E. Trim, Christopher M. Yea and Michael B. Roc. Non-peptide oxytocin agonists. Bioorganic & Medicinal Chemistry Letters 14 (2004) 4585-4589.

Reymond-Marron, 1., Tribollet, E. & Raggenbass, M. The vasopressin-induced excitation of hypoglossal and facial motoneurons in young rats is mediated by V1a but not V1b receptors, and is independent of intracellular calcium signalling. Eur J Neurosci 24, 1565-1574 (2006).

Ring R H, Schechter L E, Leonard S K, Dwyer J M, Platt B J, Graf R, Grauer S, Pulicicchio C, Resnick L, Rahman Z, Sukoff Rizzo S J, Luo B, Beyer C E, Logue S F, Marquis K L, Hughes Z A, Rosenzweig-Lipson S. Receptor and behavioral pharmacology of WAY-267464, a non-peptide oxytocin receptor agonist. Neuropharmacology. 2010 January; 58(1):69-77. Epub 2009 Jul. 15.

Saito, O., Yamamoto, T. & Mizuno, Y. Epidural anesthetic management using ropivacaine in a parturient with multi-minicore disease and susceptibility to malignant hyperthermia. J Anesth 21, 113 (2007).

Sahoo, T., D. del Gaudio, et al. (2008). "Prader-Willi phenotype caused by paternal deficiency for the HBII-85 C/D box small nucleolar RNA cluster." Nat Genet 40(6): 719-21.

Serradeil-Le Gal Claudine, Ge'rard Valette, Loï"c Foulon, Guy Germain, Charles Advenier, Emmanuel Naline, Marc Bardou, Jean-Pierre Martinolle, Brigitte Pouzct, Danielle Raufaste, Corinne Garcia, Ele'onore Double-Cazanave, Maxime Pauly, Marc Pascal, Alain Barbier, Bernard Scatton, Jean-Pierre Maffrand, and Ge'rard Le Fur. SSR126768A (4-Chloro-3-[(3R)-( )-5-chloro-1-(2,4-dimethoxybenzyl)-3-methyl-2-oxo-2,3-dihydro-1H-indol-3-yl]-N-ethyl-N-(3-pyridylmethyl)-benzamide, Hydrochloride): A New Selective and Orally Active Oxytocin Receptor Antagonist for the Prevention of Preterm Labor. JPET 309:414-424, 2004.

Swaab, D. F. (1997). "Prader-Willi syndrome and the hypothalamus." Acta Paediatr Suppl 423: 50-4.

Serradeil-Le Gal, C., et al. SSR126768A (4-chloro-3-[(3R)-(+)-5-chloro-1-(2,4-dimethoxybenzyl)-3-methyl-2-oxo-2,3-dihydro-1H-indol-3-yl]-N-ethyl-N-(3-pyridylmethyl)-benzamide, hydrochloride): a new selective and orally active oxytocin receptor antagonist for the prevention of preterm labor. J Pharmacol Exp Ther 309, 414-424 (2004).

Su L L, Chong Y S, Samuel M. Oxytocin agonists for preventing postpartum haemorrhage. Cochrane Database Syst Rev. 2007 Jul. 18; (3):CD005457.

C. Vela, z. Diaz-cabialc, c. Parrado, m. Narvacz, r. Covenas, j. a. Narvacz. Involvement of oxytocin in the nucleus tractus solitarII on central cardiovascular control: interactions with glutamate. Journal of physiology and pharmacology 2010, 61, 1, 59-65.

Whitnall, M. H., Key, S., Ben-Barak, Y., Ozato, K. & Gainer, H. Neurophysin in the hypothalamo-neurohypophysial system. II. Immunocytochemical studies of the ontogeny of oxytocinergic and vasopressinergic neurons. J Neurosci 5, 98-109 (1985).

Yamamoto, Y., et al. Neonatal manipulations of oxytocin alter expression of oxytocin and vasopressin immunoreactive cells in the paraventricular nucleus of the hypothalamus in a gender-specific manner. Neuroscience 125, 947-955 (2004).

Zelena, D., et al. Response of the adrenomedullary system to early postnatal stress in the Brattleboro rat. Ann NY Acad Sci 1148, 456-461 (2008).

Throughout this application, various references describe the state of the art to which this invention pertains. The disclosures of these references are hereby incorporated by reference into the present disclosure.

The invention claimed is:

1. A method for treating a feeding disorder with onset during neonate development in a mammal having a Magel2 deficiency or mutation, comprising the step of providing said mammal with a therapeutically effective amount of an agonist of an oxytocin receptor, wherein said feeding disorder includes a suckling deficit and is selected from the group consisting of a Prader-Willi-like syndrome or non-organic failure to thrive disease (NOFTT).

2. The method of claim 1 wherein said agonist of an oxytocin receptor is oxytocin or an active fragment thereof.

3. The method of claim 1 wherein said mammal is a human.

4. The method of claim 3 wherein said human is an infant.

5. The method of claim 4 wherein said infant is in the first three months of life.

6. The method of claim 3 wherein said human is an adult.

7. The method of claim 1 wherein said feeding disorder is Prader-Willi-like syndrome.

8. The method of claim 1 wherein said feeding disorder is NOFTT.

* * * * *